(12) United States Patent
Huang

(10) Patent No.: US 8,686,030 B2
(45) Date of Patent: Apr. 1, 2014

(54) ANTI-CANCER EXTRACT AND COMPOUNDS

(75) Inventor: Chi-Ying Huang, Taipei County (TW)

(73) Assignee: National Yang-Ming University, Taipei (TW)

( * ) Notice: Subject to any disclaimer, the term of this patent is extended or adjusted under 35 U.S.C. 154(b) by 34 days.

(21) Appl. No.: 13/249,904

(22) Filed: Sep. 30, 2011

(65) Prior Publication Data

US 2012/0259004 A1    Oct. 11, 2012

Related U.S. Application Data

(60) Provisional application No. 61/388,180, filed on Sep. 30, 2010.

(51) Int. Cl.
*A61K 31/353* (2006.01)
*C07D 407/14* (2006.01)

(52) U.S. Cl.
USPC .......................... 514/456; 549/399

(58) Field of Classification Search
USPC .......................... 514/456; 549/399
See application file for complete search history.

(56) References Cited

U.S. PATENT DOCUMENTS 7,588,776 B2 *   9/2009   Hsu ............................... 424/425

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner* — Kristin Vajda
(74) *Attorney, Agent, or Firm* — Ditthavong Mori & Steiner, P.C.

(57) ABSTRACT

The preset invention relates to a new approach for treating a cancer or fibrosis, such as Hepatocellular carcinoma, or liver fibrosis using an extract from a plant of *Graptopetalum* sp., *Rhodiola* sp. or *Echeveria* sp., and prepared by extracting the plant with Dimethyl sulfoxide (DMSO), its fraction or the compound isolated from the extract.

10 Claims, 22 Drawing Sheets

ANTI-CANCER EXTRACT AND COMPOUNDS

FIELD OF THE INVENTION

The present invention relates to a new extract and new compounds having anti-cancer activities from a plant.

BACKGROUND OF THE INVENTION

*Graptopetalum paraguayense* (GP) is a Chinese traditional herb and possesses several health benefits. According to its archaic Chinese prescription, GP is considered to have potentially beneficial effects by alleviating hepatic disorders, lowering blood pressure, whitening skin, relieving pain and infections, inhibiting inflammation, and improving brain function.

It was shown in the studies that the leaf extracts of GP could inhibit tyrosinase and angiotensin-converting enzyme activities and scavenge free radicals in vitro (Chen, S-J et al., Studies on the inhibitory effect of *Graptopetalum paraguayense* E. Walther extracts on the angiotensin converting enzyme. Food Chemistry 100:1032-1036, 2007; Chung, Y-C et al., Studies on the antioxidative activity of *Graptopetalum paraguayense* E. Walther. Food Chemistry 91:419-424, 2005; and Huang, K-F et al., Studies on the inhibitory effect of *Graptopetalum paraguayense* E. Walther extracts on mushroom tyrosinase. Food Chemistry 89:583-587, 2005.) It was found that the water and 50% ethanolic and 95% ethanolic stem extracts of GP has antioxidant activity, which were assayed for inhibitory effects on the proliferation of a human HCC cell line (HepG2) (Chen, S J et al., In vitro antioxidant and antiproliferative activity of the stem extracts from *Graptopetalum paraguayense*. Am J Chin Med 36:369-383, 2008). An in vivo research study demonstrated that the leaf extracts of GP inhibited microglia activation, oxidative stress, and iNOS expression to reduce ischemic brain injury (Kao, T K et al., *Graptopetalum paraguayense* E. Walther leaf extracts protect against brain injury in ischemic rats. Am J Chin Med 38:495-516, 2010.).

It was disclosed in U.S. Pat. No. 7,364,758 filed in 2004 by Hsu and granted in 2008 that the ethanolic extract from *Graptopetalum* had anti-liver fibrosis and anti-inflammatory effects in vivo and in vitro. Then, its continuation-in-part application, U.S. Pat. No. 7,588,776, was filed in 2008 and granted in 2009 indicating that the water-soluble fraction of *Graptopetalum* was effective in treating a liver disease or condition, such as inflammation, steatosis, and fibrosis.

SUMMARY OF THE INVENTION

The present invention relates to a new extract and its fraction, and new compounds, which are isolated from a plant, particularly *Graptopetalum* sp. The invention also provides a new approach for treating a cancer, particularly Hepatocellular carcinoma (HCC), using the new extract or the new compounds.

In one aspect, the invention provides an extract with anti-cancer activity, which is extracted with Dimethyl sulfoxide (DMSO) from a plant selected from the group consisting of *Graptopetalum* sp., *Rhodiola* sp. and *Echeveria* sp. It is unexpectedly found in the present invention that the DMSO extract has anti-cancer activity.

In one embodiment of the invention, the plant is *Graptopetalum paraguayense* or *Rhodiola rosea*. In one example of the invention, the extract is obtained by extracting the plant with 30% DMSO.

In another aspect, the invention provides a fraction containing rich anti-cancer components from a plant selected from the group consisting of *Graptopetalum* sp., *Rhodiola* sp. and *Echeveria* sp, particularly *Graptopetalum paraguayense* or *Rhodiola rosea*, which is prepared by extracting the plant with Dimethyl sulfoxide (DMSO), and then isolating by chromatography to obtain a fraction called as HH-F3, which has effects in causing cytotoxicity and down-regulating AURKA, AURKB, and FLJ10540 expression in cancer cells.

In one embodiment of the invention, a Sephadex LH-20 column was used for chromatography column. According to the invention, the fraction according to the invention has high cytotoxicity effects and is effective in down-regulating AURKA, AURKB, and FLJ10540 expression in Huh7 and HepG2 cells.

In the mechanistic study on the fraction HH-F3, it was found that the fraction HH-F3 induced HCC to undergo apoptosis. In other words. It was indicated that the fraction HH-F3 has a therapeutic effect on cancer cells, particularly HCC.

In a further aspect, the invention provides a compound, having a structure of formula I below,

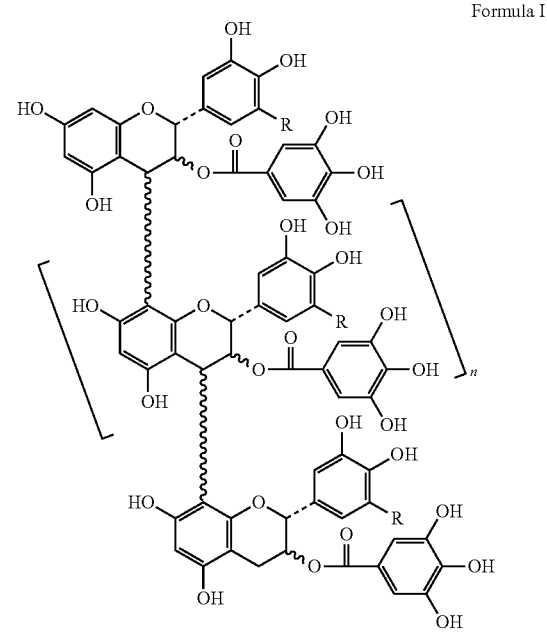

Formula I wherein one of the Rs is H, or prucyanidin (PC) unit; and the other is OH or prodelphindine (PD) unit; n is a number ranging from 21 to 38; and PC unit:PD unit<1:20. The structure of prucyanidin (PC) unit is

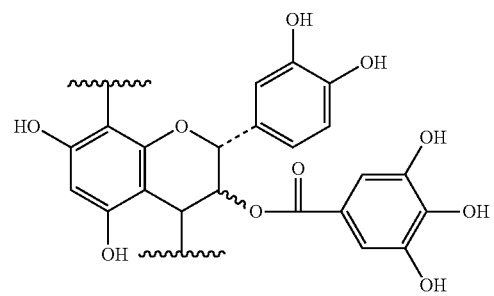 [SMILES: *c1c(O)cc(O)c2c1O[C@H](c1ccc(O)c(O)c1)C(OC(=O)c1cc(O)c(O)c(O)c1)C2*]

and the structure of prodelphindine (PD) is

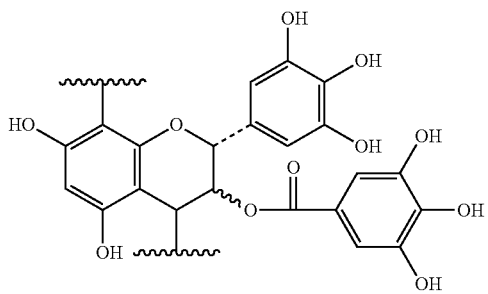 [SMILES: *c1c(O)cc(O)c2c1O[C@H](c1cc(O)c(O)c(O)c1)C(OC(=O)c1cc(O)c(O)c(O)c1)C2*]

According to the invention, the compound of formula I can be isolated from a plant selected from the group consisting of *Graptopetalum* sp., *Rhodiola* sp. or *Echeveria* sp. In one embodiment of the invention, the compound was purified from the fraction of *Graptopetalum paraguayense* or *Rhodiola rosea*. It was found that the compound of formula I is rich in 3,4,5-trihydroxy benzylic moieties, and has anti-cancer activities.

In yet aspect, the invention provides a composition or a pharmaceutical composition, comprising the extract, the fraction or the compound of the invention, and a pharmaceutically acceptable carrier. Furthermore, the pharmaceutical composition has anti-cancer activity, which is effective in the prevention or treatment of an cancer, such as liver cancer particularly HCC.

In further yet aspect, the invention provides the use of the extract, the fraction or the compound of formula I of the invention in manufacture of a medicament for treating a cancer, particularly, HCC.

In further more aspect, the invention provides a method for preventing or treating a cancer, comprising administrating a subject in need thereof with an therapeutically effective amount of the extract, the fraction or the compound of the invention. In one example of the invention, the cancer is HCC.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings the embodiments which are presently preferred. It should be understood, however, that the invention is not limited to the embodiments shown in the drawings.

In the drawings:

FIG. 2 shows the effects of the fraction HH-F3 according to the invention in causing an increase of cytotoxicity; wherein

FIG. 8 shows that the HH-F3 fraction down-regulates AURKA and FLJ10540 in HCC cell lines and activated hepatic stellate cells; including

FIG. 9 shows the effect of the fraction HH-F3 in causing apoptosis in HCC cell lines; wherein Huh7 and Mahlavu cells were treated with 5, 25, and 50 μg/ml HH-F3 for 24 and 48 hours. After treatment with the HH-F3 fraction for 24 and 48 hours, the cell lysates were subjected to immunoblot analysis for anti-cleaved caspase-3 and cleaved PARP.

FIG. 10 shows the effect of the fraction HH-F3 in decreasing mitochondrial membrane potential and increasing ROS generation in the HCC cell lines, including

DESCRIPTION OF THE INVENTION

Figure 1:
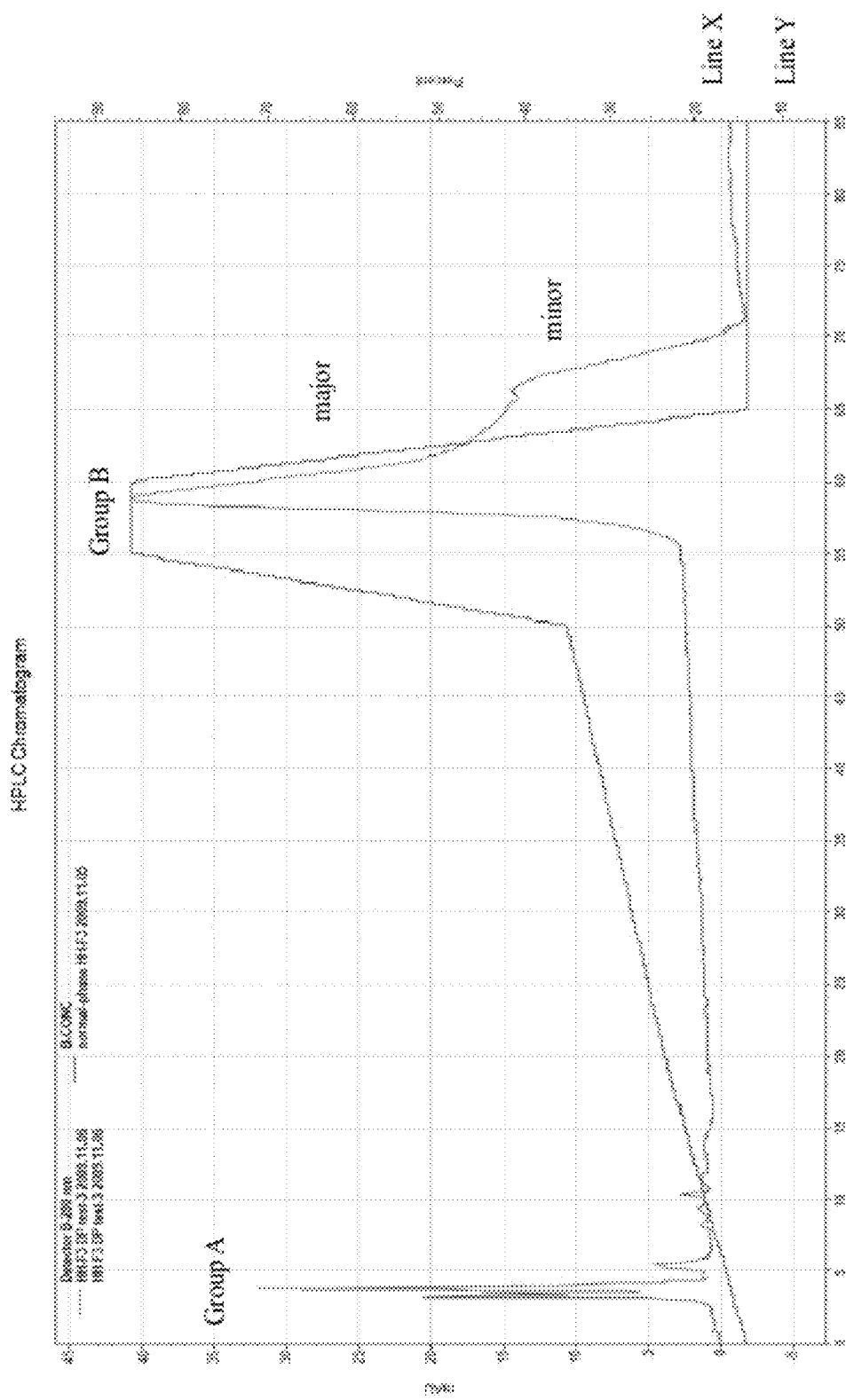
FIG. 1 provides a HPLC fingerprint of the fraction HH-F3 according to the invention, wherein the chromatogram and the elution gradient curve were marked as Line X and Line Y, respectively.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The invention provides a new extract a plant selected from the group consisting of *Graptopetalum* sp., *Rhodiola* sp. or *Echeveria* sp., prepared by extracting the plant with DMSO, referred to as the GP extract. It is unexpectedly found in the present invention that the GP extract has anti-cancer activity.

According to the invention, the extract may be prepared by extracting the plant with Dimethyl sulfoxide (DMSO) using commonly used or standard methods in this art. In one example of the invention, the leaves of the plant are grounded and lypholized into powder and vortexed with DMSO, preferably 30% DMSO. A further extraction with methanol (MeOH) may be included before the extraction with DMSO.

The term "*Graptopetalum*", as used herein, refers to any plant in the genus of *Graptopetalum*, or part or parts thereof. Combinations of more than one species of *Graptopetalum*, or parts thereof, are also contemplated. The *Graptopetalum* is preferably *Graptopetalum paraguayense*.

The term "*Rhodiola*", as used herein, refers to any plant in the genus of *Rhodiola Rhodiola*, or part or parts thereof. Combinations of more than one species of *Rhodiola*, or parts thereof, are also contemplated. The *Rhodiola* is preferably *Rhodiola rosea*.

The term "*Echeveria*", as used herein, refers to any plant in the genus of *Echeveria*, or part or parts thereof. Combinations of more than one species of *Echeveria*, or parts thereof, are also contemplated. The *Echeveria* is preferably *Echeveria peacockii*.

In one preferred embodiment of the invention, the plant is *Graptopetalum paraguayense* or *Rhodiola rosea*.

The term "extract" as used herein refers to a solution obtained by soaking or mixing a substance to be extracted with a solvent. In the present invention, the extract is a DMSO extract.

The invention also provides a fraction containing rich anti-cancer components from a plant selected from the group consisting of *Graptopetalum* sp., *Rhodiola* sp. and *Echeveria* sp, which is prepared by extracting the plant with Dimethyl sulfoxide (DMSO), and then isolating by chromatography to obtain a fraction called as HH-F3. In one example of the invention, the plant is *Graptopetalum paraguayense* or *Rhodiola rosea*. The fraction is obtained by extracting the plant with DMSO and isolating by chromatography to obtain a fraction, referred to as HH-F3. In one example of the invention, a Sephadex LH-20 column is used for chromatography. It was found that the fraction has effects in causing cytotoxicity and down-regulating AURKA, AURKB, and FLJ10540 expression in cancer cells, particularly the HCC cell lines such as Huh7 and HepG2 cells. A mechanistic study of the fraction HH-F3 was performed and it was indicated that the fraction HH-F3 induced HCC to undergo apoptosis. Accordingly, the fraction HH-F3 is a potential therapeutic agent for the prevention or treatment of a cancer, particularly liver cancer, such as HCC.

According to one example of the invention, a sub-fraction referred to as HH-F3a was obtained from the fraction HH-F3 via dialysis. Then, the active compounds were isolated from the HH-F3a fraction, which is different from the known proanthocyanidin compounds. The compound as obtained is a proanthocyanidin rich in 3,4,5-trihydroxy benzylic moieties. The compound is of a structure of formula I below,

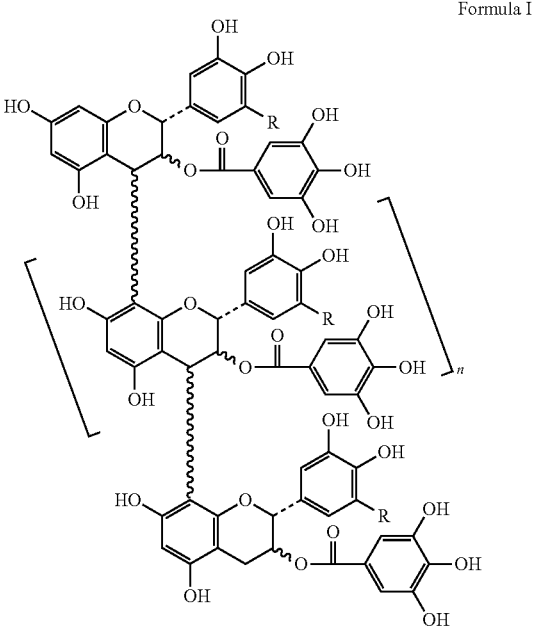

Formula I wherein one of the Rs is H, or prucyanidin (PC) unit; and the other is OH or prodelphindine (PD) unit; n is a number ranging from 21 to 38; and PC unit:PD unit<1:20. The structure of prucyanidin (PC) unit is

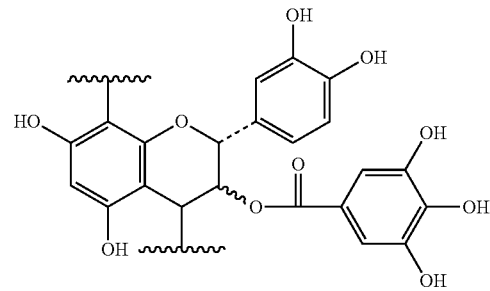 [SMILES: *c1c(O)cc(O)c2c1O[C@H](c1ccc(O)c(O)c1)C(OC(=O)c1cc(O)c(O)c(O)c1)C2*]

and the structure of prodelphindine (PD) is

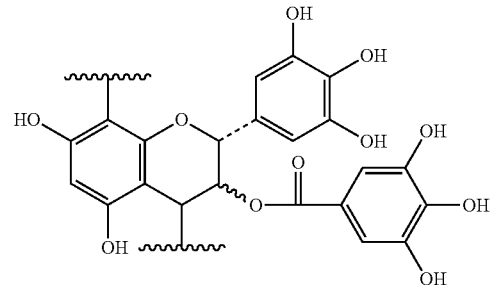 [SMILES: *c1c(O)cc(O)c2c1O[C@H](c1cc(O)c(O)c(O)c1)C(OC(=O)c1cc(O)c(O)c(O)c1)C2*]

Accordingly, the invention provides the compound of formula I, which is proved to have anti-cancer activity. In one example to the invention, the compound of formula I was obtained by a extraction from the plant of *Graptopetalum* sp., *Rhodiola* sp. or *Echeveria* sp. with DMSO to obtain a DMSO extract, a selection from the DMSO extract using down-regulation of AURKA via western blot to obtain a sub-fraction referred to as "HH-F3a" via dialysis, and a further purification.

The invention provides a pharmaceutical composition, comprising a therapeutically effect amount of the extract, the fraction or the compound of formula I of the invention, and a pharmaceutically acceptable carrier.

The term "therapeutically effective amount" as used herein refers to an amount of an agent sufficient to achieve the intended purpose for treatment. For example, an effective amount of *Graptopetalum* to treat HCC is an amount sufficient to kill HCC cells. The therapeutically effective amount of a given agent will vary with factors such as the nature of the agent, the route of administration, the size and species of the animal to receive the agent, and the purpose of the administration. The therapeutically effective amount in each individual case may be determined empirically by a skilled artisan according to the disclosure herein and established methods in the art.

The pharmaceutical composition of the invention may be administered in any route that is appropriate, including but not limited to parenteral or oral administration. The pharmaceutical compositions for parenteral administration include solutions, suspensions, emulsions, and solid injectable compositions that are dissolved or suspended in a solvent immediately before use. The injections may be prepared by dissolving, suspending or emulsifying one or more of the active ingredients in a diluent. Examples of said diluents are distilled water for injection, physiological saline, vegetable oil, alcohol, and a combination thereof. Further, the injections may contain stabilizers, solubilizers, suspending agents, emulsifiers, soothing agents, buffers, preservatives, etc. The injections, are sterilized in the final formulation step or prepared by sterile procedure. The pharmaceutical composition of the invention may also be formulated into a sterile solid preparation, for example, by freeze-drying, and may be used after sterilized or dissolved in sterile injectable water or other sterile diluent(s) immediately before use.

According to the invention, the composition may also be administered through oral route, wherein the composition may be in a solid or liquid form. The solid compositions include tablets, pills, capsules, dispersible powders, granules, and the like. The oral compositions also include gargles which are to be stuck to oral cavity and sublingual tablets. The capsules include hard capsules and soft capsules. In such solid compositions for oral use, one or more of the active compound(s) may be admixed solely or with diluents, binders, disintegrators, lubricants, stabilizers, solubilizers, and then formulated into a preparation in a conventional manner. When necessary, such preparations may be coated with a coating agent, or they may be coated with two or more coating layers. On the other hand, the liquid compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

It was confirmed in the examples that the extract, the fraction or the compound of the invention, or the pharmaceutical composition thereof caused an apoptosis in HCC cells, suggesting that they have anti-cancer activity, which may be used for the prevention or treatment of a cancer, particularly HCC. On the other hand, it is suggested that they are effective in treatment fibrosis, particularly Liver fibrosis.

Accordingly, the invention provides the use of the extract, the fraction or the compound of formula I of the invention in manufacture of a medicament for treating a cancer, particularly, HCC. On the other hand, the invention provides a method for preventing or treating a cancer or fibrosis comprising administrating a subject in need thereof with an therapeutically effective amount of the extract, the fraction or the compound of the invention, particularly HCC and liver fibrosis.

The following examples are offered to illustrate this invention and are not to be construed in any way as limiting the scope of the present invention.

EXAMPLE

Example 1

Extraction and Purification from GP or *Rhodiola rosea*

The leaves of *Graptopetalum paraguayense* (referred to as GP) were ground and lyophilized into powder at −20° C. and stored in a moisture buster at 25° C. before extraction. First, 1.5 g GP powder was vortexed with 10 ml 100% methanol (MeOH) for 5 minutes and then centrifuged at 1500 g for 5 minutes. After removal of the supernatant, 10 ml $H_2O$, 100% acetone, 100% methanol, 100% ethanol, 70% ethanol, 50% ethanol, 100% DMSO and 30% DMSO was added to each pellet to resuspend them for each extract. The suspension was mixed by vortexing for 5 minutes, centrifuged twice at 1500 g for 5 minutes, centrifuged again at 9300 g for 5 minutes, and filtered using a 0.45 μm filter by laminar flow at room temperature. The 30% DMSO supernatant was either fractionated into four fractions (F1-F4) by a Sephadex LH-20 column or stored at −20° C. as a 150 mg/ml stock solution (referred to as 30% DMSO GP extracts). The GP extract or the fraction HH-F3 was also subjected to dialysis against water by a dialysis membrane (MWCO 12-14,000) (Spectrum Laboratories, Rancho Dominguez, Calif.) to obtain active compounds. Using the analysis of AURKA, AURKB, and FLJ10540 protein levels via Western blot, active molecules were analyzed, which we refer to as the fraction HH-F3. In addition, the fraction HH-F3 was further analyzed by HPLC and $^1$H- and $^{13}$C-NMR spectra to identify the structure of the active molecules.

Similarly, the plants of *Rhodiola rosea* (referred to as RS) were lyophilized into powder and stored in moisture buster at 25° C. before extraction. One and a half grams of RS powder was dissolved in 10 ml $H_2O$ and then centrifuged at 1500 g for 5 minutes, followed by filtering using a 0.45 μm filter by laminar flow at room temperature. The samples were stored at −20° C. as 150 mg/ml stock solutions.

Figure 6A:
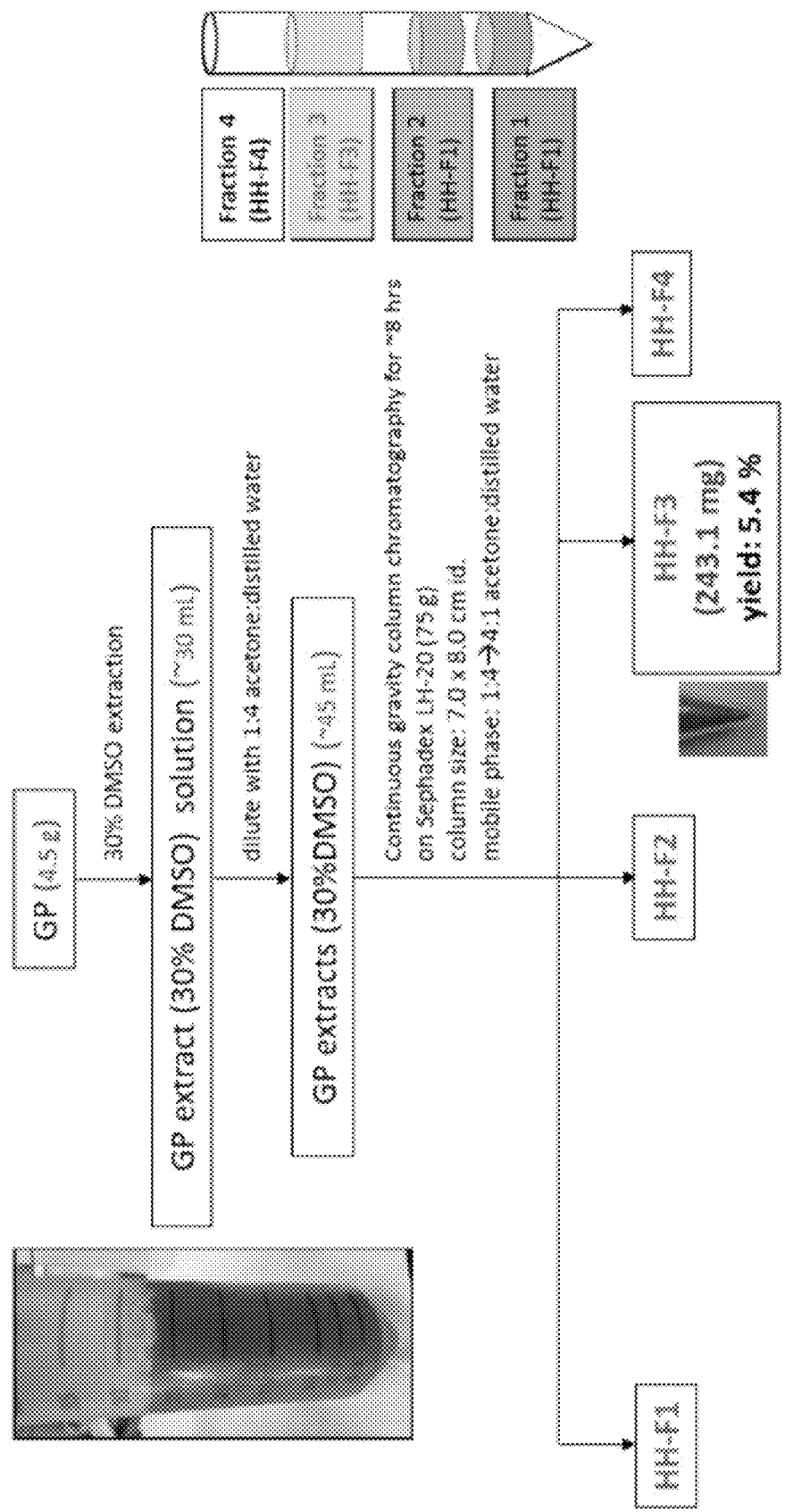
FIG. 6 shows the effects of the different purification fractions of GP on AURKA protein expression in the HCC cell lines; including FIG. 6(A) illustrating the purification scheme of the GP extract and fraction HH-F3 according to the invention.
FIG. 6(B) shows that HepG2 cells were treated with the 30% DMSO GP extracts, HH-F1, HH-F2, HH-F3, and HH-F4 for 3 hours. AURKA and AURKB expression levels were not suppressed by treatment with the HH-F1, HH-F2 and HH-F4 fractions in HepG2 cells.
FIG. 6(C) shows that the expression of AURKA was inhibited after treatment with the 30% DMSO GP extracts and the HH-F3 fraction.
FIG. 6(D) shows that the expression of AURKA was inhibited after treatment with the HH-F3 a fraction.
Figure 6B:
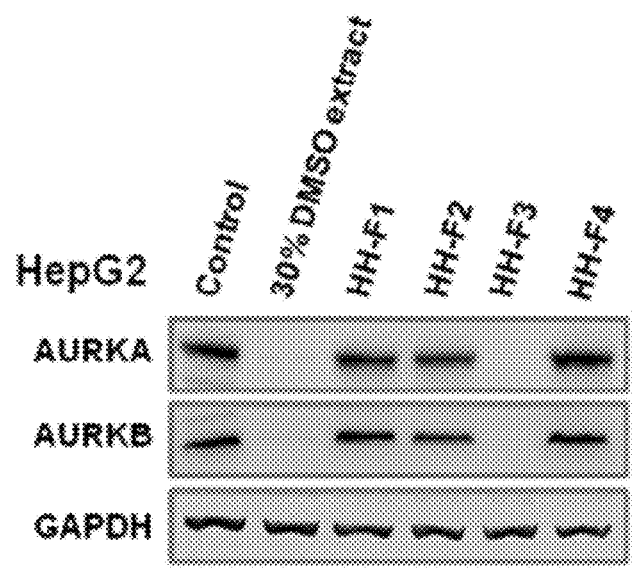
Figure 6C:
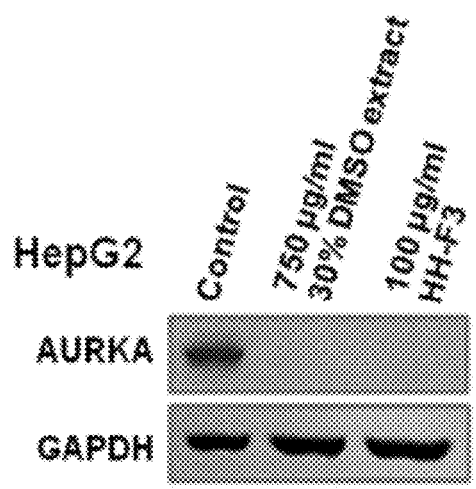
Figure 6D:
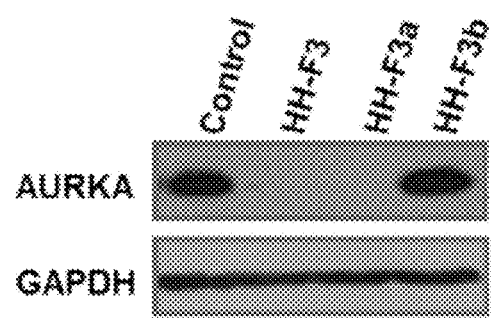

A chemical investigation on the fraction HH-F3 of the invention resulted in the identification of its major components as polyphenolic compounds, according to broadened aromatic signals in the $^1$H and $^{13}$C NMR spectra. The major compounds in the HH-F3 fraction were identified to be tannins because of their characteristic pink color with partial silver metal-like luster after lyophilization. The total tannin content of the HH-F3 fraction was approximately 68%, as determined by a colorimetric assay for condensed tannin quantification, which used catechin as the standard when monitored at $OD_{500}$. The HPLC fingerprint of the HH-F3 fraction (FIG. 1) revealed that two groups of compounds (Groups A and B) with distinct molecular weight ranges existed in the HH-F3 fraction, and one major and one minor component were detected in Group B. A proanthocyanidin-rich high molecular weight fraction, HH-F3a (with a yield of 71.9% compared to the amount of the starting material HH-F3), was prepared from the HH-F3 fraction using dialysis. Briefly, HH-F3 (112.1 mg) was dialyzed by a dialysis membrane (MWCO 12-14,000) against water to give an inner membrane fraction (HH-F3A, 80.6 mg) and an outer-membrane fraction (7.4 mg). This fraction contained the active compounds, as determined by measuring the disappearance of AURKA by Western blot (FIG. 6D). The main skeleton for the proanthocyanidin fraction of HH-F3a was determined to be a proanthocyanidin polymer (see below), and its physio-chemical properties, including the mean molecular weight (mMW), mean degree of polymerization (mDP), PC:PD ratio and stereochemistry (cis:trans), are listed in Table 1. mMW and mDP were determined by analyzing the ratio of the degraded terminal and elongating monomers. In addition, to simplify the preparation protocols, another method via directly dialysis of GP extracts against water (Method II) was performed, and the physiochemical data of the compounds prepared by Method II are also listed in Table 1. The listed physiochemical properties in Table 1 suggest that the fraction prepared by Method II was identical to that of Method I (the method used to prepare HH-F3a).

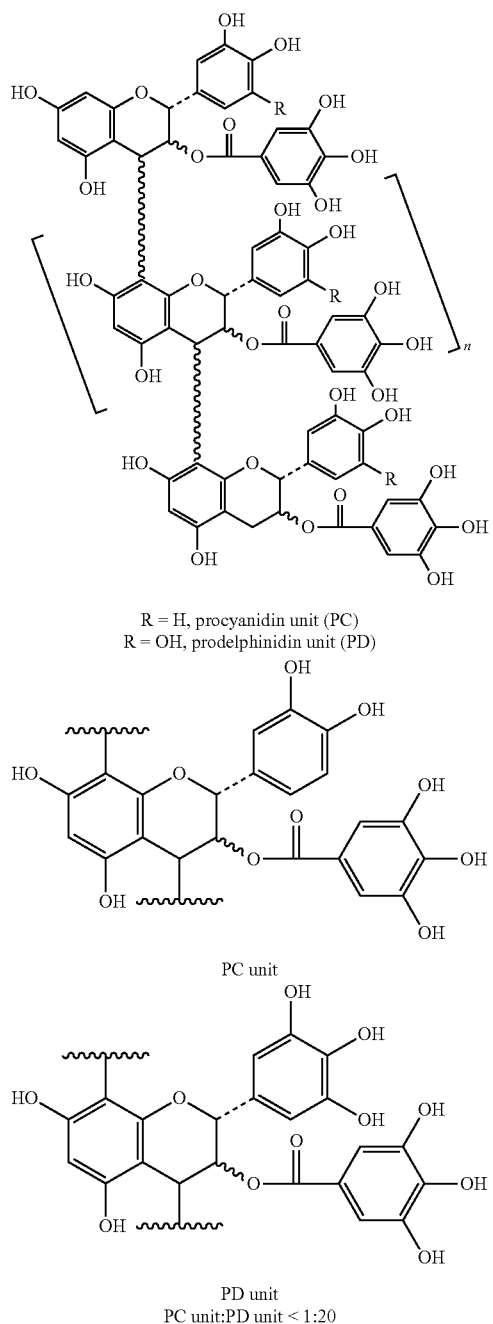

R = H, procyanidin unit (PC)
R = OH, prodelphinidin unit (PD)

PC unit

PD unit
PC unit:PD unit < 1:20

Predicted structure of HH-F3a: a polymeric proanthocyanidin with high prodelphinidin ratio (>95%) (21<n<38)

TABLE 1

Physiochemical properties for the proanthocyanidin polymer of formula 1 according to the invention

| Preparation | PC:PD | Cis:trans | 3-O-galloyl | mDP | mMW (kD) |
|---|---|---|---|---|---|
| Method I | <1:20 | 2,3-cis 3,4-trans | >95% | 40 | 18 |
| Method II | <1:20 | 2,3-cis 3,4-trans | >95% | 40 | 18 |

[1]The method that prepared HH-F3a (by Sephadex LH-20 chromatography)
[2]by dialysis Since no polymeric compound from GP has been reported, the polyphenolic compounds from another precious Crassulaceous herb *Rhodiola rosea* (golden root) are utilized as reference compounds for structural identification of HH-F3a. *R. rosea* has been reported to have polymeric proanthocyanidin (PAC). The structure of the main compounds in the HH-F3a fraction was very similar to the proanthocyanidin compounds of *R. rosea* (see Table 2) but with rather minor signals (<5%) for a procyanidin unit (PC unit), which was not detectable in the $^{13}$C NMR spectrum ($\delta_C$ 114 ppm, B ring C-2' and C-5'). In addition, the PAC compounds are frequently found in many common grape species, such as *Vitis vinifera*. Thus, the PACs from *V. vinifera* are also brought into comparison. Table 2 shows the physiochemical properties for the proanthocyanidin polymers from *R. rosea* and *V. vinifera* (a common grape species). Compared to the data in Table 2, the proanthocyanidin compound in the HH-F3a fraction was within 2.5× of the PD to PC ratio, 3.0× of the mDP and mMW for *R. rosea*, and 30 to 80×, 1.1 to 4.9×, and 4.7 to 41.3× higher than the mDP, mMW and % of 3-O-galloyl for *V. vinifera*. To the best of our knowledge, no proanthocyanidin compound from GP has been isolated, and no proanthocyanidin compound with identical physiochemical properties has been reported. This evidence suggests that the proanthocyanidin compound found in the HH-F3a fraction is a new compound that is rich in 3,4,5-trihydroxy benzylic moieties (including a B ring of the PD unit and gallic acid), very similar to that found in *R. rosea* but much higher than that found in grape skin and seed.

TABLE 2

Physiochemical properties for known proanthocyanidin polymers

| Source | PC:PD | cis:trans | 3-O-galloyl (%) | mDP | mMW (kD) |
|---|---|---|---|---|---|
| *Rhodiola rosea* | 1:8 | 2,3-cis 3,4-trans | >95 | 13.3 | 6.0 |
| Seed of *Vitis vinifera*[1] | 4:1 | 2,3-cis | 20.4 | 8.1 | 2.6 |
| Skin of *Vitis vinifera* | 3:2 | 2,3-cis | 2.3 | 34.9 | 10.4 |

[1]The European grapevine native to the Mediterranean and Central Asia

Example 3

Effect Examples

1. Viability Assay

The cells were seeded in 24-well plates (4,000-5,000 cells/well), incubated overnight and then treated with the 30% DMSO GP extract or the HH-F3 fraction for 0, 24, 48, or 72 hours. After treatment, the cells were gently washed 3 times with 1×PBS (137 mM NaCl, 2.7 mM KCl, 10 mM $Na_2HPO_4$, 2 mM $KH_2PO_4$) and then were incubated with 0.5 μg/ml 3-(4,5-cimethylthiazol-2-yl)-2,5-diphenyl tetrazolium bromide (MTT) for 2 hours. The medium was removed, and the deep-blue crystals were dissolved with 100% DMSO at room temperature for 10 minutes. OD values were measured at 570 nm with an ELISA reader.

2. Western Blot

All samples were denatured by heating at 95° C. for 10 minutes and resolved by 8% or 10% SDS-polyacrylamide gel electrophoresis (SDS-PAGE) at 80 V and 100 V for the stacking and running gel, respectively. After SDS-PAGE, the proteins were transferred to polyvinylidene difluoride (PVDF) membranes using the Bio-Rad transfer system. After the proteins were transferred, the membranes were stained with Ponceau S to confirm the efficiency and uniformity of the protein transfer. The membranes were blocked with 5% non-fat skim milk (BD) at room temperature for 30 minutes and then were incubated with primary antibody at 4° C. overnight. Afterward, the membranes were washed with 1× Tris-buffered saline Tween-20 (TBST) three times (10 minutes each). The membranes were incubated with secondary antibody for 2 hours. Then, they were washed with 1×TBST three times (10 minutes each). The signals of the secondary antibodies were visualized by adding HRP substrate peroxide solution/luminol reagents (Immobilon™ Western Chemiluminescent Substrate, Millipore; mixed at a 1:1 ratio) and were detected by the Fujifilm LAS4000 luminescent image analysis system.

3. Cell Counting

The cells were seeded in 12-well plates (10,000-30,000 cells/well) overnight and then were treated with the HH-F3 fraction for 0, 24, 48, or 72 hours. The cells were trypsinized and then counted after mixing with 0.4% trypan blue.

4. Cell Cycle Analysis and Flow Cytometry

After trypsinizing the cells and washing with 1×PBS 3 times, the cells were centrifuged at 800 g for 5 minutes. Then, the cells were resuspended in 70% ethanol in PBS and kept at −20° C. for more than 16 hours. After centrifugation at 800 g for 5 minutes, the cell pellets were resuspended with cold PBS containing 100 µg/ml RNAse A (Sigma-Aldrich) for 20 minutes. Then, the cells were stained with 20 µg/ml propidium iodide (PI, Sigma-Aldrich) for 20-30 minutes, and the DNA content was measured by the BD FACSCanto and analyzed by FlowJo software.

5. Mitochondrial Membrane Potential Assay

Mitochondrial membrane potential was analyzed using 5, 5', 6, 6'-tetrachloro-1, 1', 3, 3'-tetraethylbenzimidazolcarbocyanine iodide (JC-1), which was purchased from Cayman Chemical Co. The cultured cells were seeded in 96-well black plates at a density of 7000 cells/well and incubated overnight, then treated with or without the HH-F3 fraction for 48 hours. The JC-1 staining solution was added to each well and mixed gently at 37° C. for 15-30 minutes in the dark. The plates were centrifuged at 400 g at room temperature for 5 minutes, and the supernatant was removed. Then, JC-1 assay buffer was added to each well, followed by centrifugation at 400 g at room temperature for 5 minutes, after which the supernatant was removed. Finally, JC-1 assay buffer was added to each well for analysis using a fluorescent plate reader.

6. Measurement of ROS Levels

Intracellular generation of superoxide radicals ($O_2^-$) was assessed by hydroethidine fluorescence (AAT Bioquest, Inc.). The cells were treated with or without the HH-F3 fraction for 48 hours. Hydroethidine (10 µM) was added to each well and was mixed gently for 30-60 minutes at 37° C. in the dark. Cellular fluorescence was monitored at wavelengths of 520 nm (excitation) and 610 nm (emission).

Intracellular peroxide levels were determined with dichlorofluorescein (DCFH) diacetate (Marker Gene Technologies, Inc.). Following treatment with the HH-F3 fraction for 48 hours, the medium was aspirated, and the cells were washed twice with PBS. Then, the cells were incubated with DCFH at a final concentration of 20 µM in serum-free media for 30-60 min at 37° C. in the dark. The cells were washed again with PBS and maintained in 200 µl of culture media. Cellular fluorescence was monitored at wavelengths of 485 nm (excitation) and 528 nm (emission).

7. Animals and the Experimental Environment

A total of 120 male Wistar albino rats (150-180 g) that 6 weeks of age at the start of the experimental period were used. All animals were fed ad libitum with standard chow and water during the study and were acclimated for 7 days before disease induction.

Experimental Protocol

The rats were randomly divided into the normal group (N=10), the diethylnitrosamine (DEN) group (N=30), the low-dose GP group (N=30) and the high-dose GP group (N=30). We included another 5 rats for the HH-F3-treated group. In all groups except the normal group, the rats drank an aqueous solution of 100 ppm (v/v) DEN (Sigma-Aldrich, St. Louis, Mo., USA) daily as the sole source of drinking water for 63 days, and starting on day 64, they were fed tap water for another 14 days. DEN solution was prepared each week and consisted of an individualized dose according to the weight gain/loss of the animal in response to the previous dose. Visible liver tumors were noted after day 42, and liver fibrosis was observed after day 63. During the experimental period, the animals were weighed weekly to calculate weight gain, and the amount of water consumption was also measured every week. In the low-dose group, the rats received 0.6 g/rat lyophilized GP powder, and in the high-dose group, the rats received 1.8 g/rat lyophilized GP powder daily beginning on day 42 for 3 weeks.

Harvesting Procedure and Morphologic Evaluation of the Liver

All animals were euthanized on the day 84. The animals were fasted overnight and then sacrificed by $CO_2$ inhalation. After the rats were sacrificed, the bodies, livers and spleens were weighed, and the conditions of the organs were recorded after necropsy, which followed a midline laparotomy. All lobes of the liver were promptly harvested and thoroughly examined to clarify the nature of the liver surface and the development of liver foci, persistent nodules (PNs), or cancer at every time point; subsequently, the liver was cut into 5-mm sections. All macroscopically visible nodules were counted on the liver surface and in the 5-mm sections to determine their number and size.

Tumor Burden Assessment

To establish the course of tumor development in the animals fed with DEN, all lobes of the liver were promptly harvested, and all macroscopically visible nodules were counted on the liver surface and in the 5 mm sliced sections to determine their numbers and sizes. Tumor burdens were determined by estimating the sums of the volumes of all tumor nodules with diameters greater than 3 mm for each animal and then comparing the groups.

Bile Flow Rate

Bile flow rate was measured prior to the sacrifice of the animals after deep anesthesia with 80 mg/kg ketamine. To measure the bile flow rate, a PE10 silicon tube was placed in the common bile duct and then connected with a calculated polyethylene tube. Bile flow in the tube was measured at 5-min intervals.

Histopathological Evaluation

After draining the blood, tissue slices of approximately 5-mm thickness that contained tumors were dissected from each lobe of the liver. Sections with thicknesses of 5 µm were cut and stained with hematoxylin and eosin for histopathological analysis using published diagnostic criteria.

Immunohistochemical Staining for α-Smooth Muscle Actin (α-SMA)

The liver samples were fixed with formalin, embedded with paraffin, and then sectioned into 5 µm sections. The sections were deparaffinized, rehydrated and then treated with 0.03% hydrogen peroxide for 10 minutes to quench endogenous peroxidase activity. Following two washes with PBS, the sections were incubated for 1 h at room temperature with a mouse anti-human α-SMA monoclonal antibody (1:50 dilution, DakoCytomation, Denmark). For α-SMA staining, the sections were washed and further incubated with a secondary antibody, rabbit anti-mouse IgG (1:200 dilution), at room temperature for 1 hour. The sections were then developed similarly. After staining, the sections were counterstained with hematoxylin for microscopic examination. The percentage of α-SMA-positive area ($mm^2/cm^2$ of liver section) was measured using the Digital Camera System HC-2500 (Fuji Photo Film), Adobe Photoshop version 5.0J, and Image-Pro Plus version 3.0.1J.

Assay of Hydroxyproline Content in the Liver

Liver specimens were weighed, and 20 mg of the frozen samples was hydrolyzed in 20 ml of 6 N HCl and carefully ground. Additionally, 6 N HCl was then added to obtain a total volume of 30 ml per mg tissue. The ground tissue in HCl was hydrolyzed at 120° C. for 16 h. After brief cooling on ice and centrifugation at 8000 g for 10 min, the supernatant was removed and placed in a new tube; the volume lost to evaporation was replenished by water. An equal volume of 6 N NaOH was added and mixed, and the solution was adjusted to pH 4-9 using litmus paper. Forty microliters of the neutralized sample solution was added to the wells of a 96-well ELISA plate and oxidized using a solution containing 5 ml of 7% chloramine T (Sigma-Aldrich) and 20 ml of acetate/citrate buffer. Thereafter, 150 mL of Ehrlich's solution was added. The final mixture was incubated at 60° C. for 35 min and then at room temperature for another 10 min, after which the absorbance was determined at 560 nm. Standard solutions containing 100, 80, 60, 40, 20 and 0 mg/ml of authentic 4-hydroxy-L-proline (Sigma-Aldrich) were treated likewise. The standard curve was linear in this range (r=0.99). The value of the liver hydroxyproline level was expressed as hydroxyproline (mg)/wet liver weight (g). All assays were repeated in triplicate.

Immunocytochemistry for Oxidative Stress

A nitroblue tetrazolium (NBT, Sigma-Aldrich) perfusion method was used for localizing de novo ROS generation in the liver. NBT-perfused livers were removed and fixed in a zinc/formalin solution and processed for histological examination of formazan deposits. The density of blue NBT deposits was determined using Adobe Photoshop 7.0.1 image software analysis.

Results

The Effects of Different GP Preparations on Huh7 and Mahlavu Cells

Figure 2A:
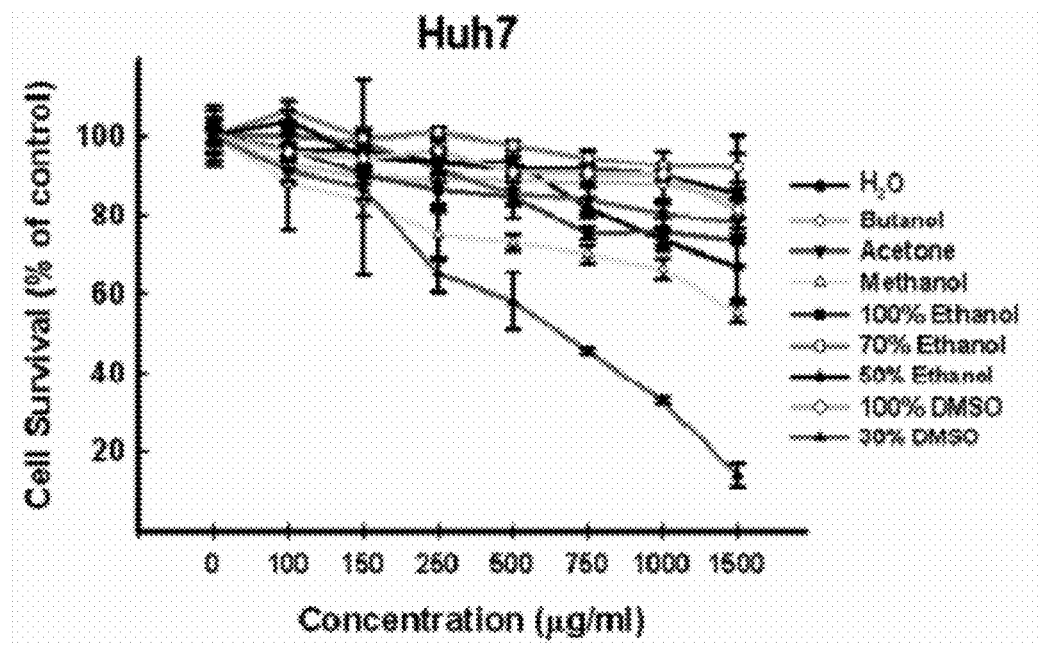
FIG. 2(A) shows the effects in Huh7.
Figure 2B:
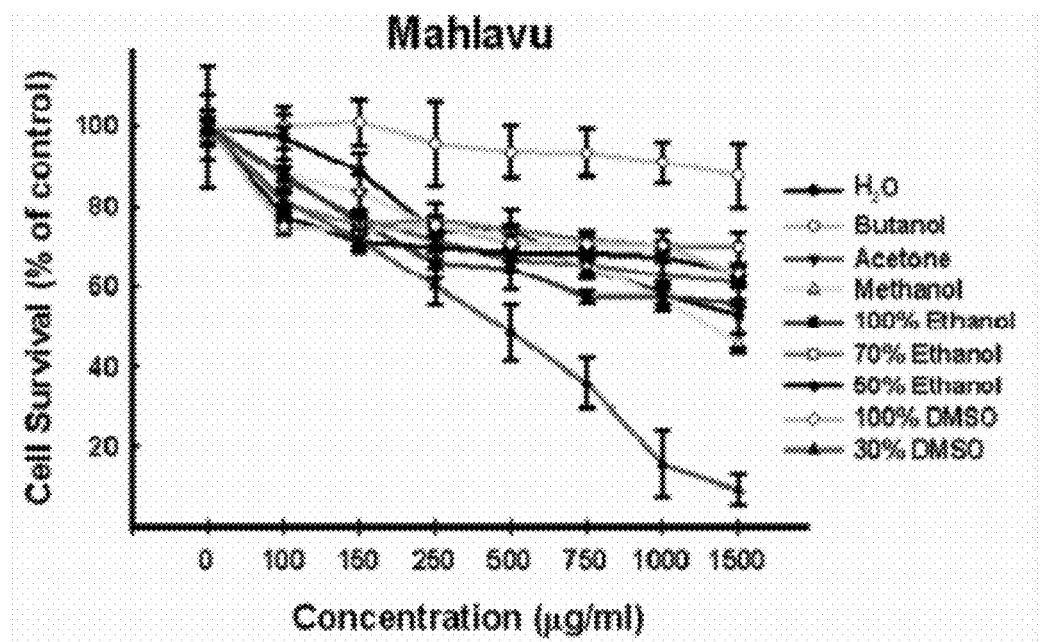
FIG. 2(B) shows the effects in Mahlavu cells, as compared with other extracts prepared from different solvents as compared with other extracts prepared from different solvents, wherein Huh7 (A) and Mahlavu (B) cells were treated with GP extracts prepared from water, acetone, methanol, 100% ethanol, 70% ethanol, 50% ethanol, 100% DMSO, and 30% DMSO at the concentrations of 100, 150, 250, 500, 750, 1000, and 1500 µg/ml for 72 hours, after which the cells were subjected to MTT assays. Of these extract preparations, the 30% DMSO GP extracts exhibited the most significant inhibition of cell viability in Huh7 and Mahlavu cells at 72 hours.

To test the potential biological effects of GP, different preparations of GP extracts, including water extract, butanol extract, acetone extract, methanol extract, 100% ethanol extract, 70% ethanol extract, 50% ethanol extract, 100% DMSO extract and 30% DMSO extract were prepared and used to treat human HCC cells. As shown in FIG. 1, the growth inhibitory effects that were caused by different preparations of the GP extracts were evaluated in a dose-dependent manner. The MTT assay results indicated that the 30% DMSO extracts significantly inhibited the viability of Huh7 (FIG. 2A) and Mahlavu (FIG. 2B) cells.

Figure 3A:
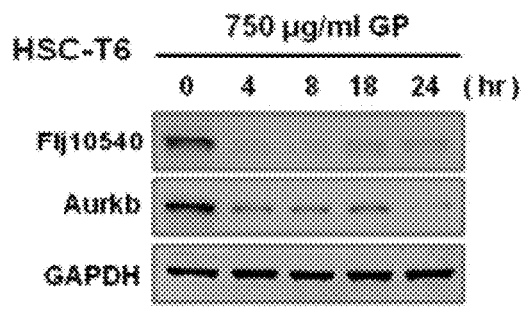
FIG. 3 shows the effects of the fraction HH-F3 according to the invention in decreasing degradation of several mitotic regulators during interphase and M phase in HSC-T6 (A), and HepG2 and Huh7 cells ((B) and (C)), wherein (A) HSC-T6 cells were treated with the 30% DMSO GP extracts. The cell lysates were subjected to immunoblot analysis with anti-F Flj10540 and anti-Aurkb antibodies; (B) HepG2 and Huh7 cells were treated with various concentrations of the 30% DMSO GP extracts; the cell lysates were subjected to immunoblot analysis with anti-FLJ10540, anti-AURKA, and anti-AURKB antibodies; (C) HepG2 and Huh7 cells were treated with 75 ng/ml nocodazole (NOC) for 16-18 hours. After pretreatment with the synchronizing agent, the cells were then treated with 750 µg/ml 30% DMSO GP extracts or vehicle control (30% DMSO) for another 3 hours; Western blots were performed using anti-F FLJ10540, anti-AURKA, and anti-AURKB antibodies; it is important to note the following: (1) AURKA, AURKB, and FLJ10540 were highly expressed in mitotic cells compared with interphase cells, and (2) the protein expression levels of AURKA, AURKB, and FLJ10540 in interphase and metaphase were both suppressed after treatment with the 30% DMSO GP extracts.
Figure 3B:
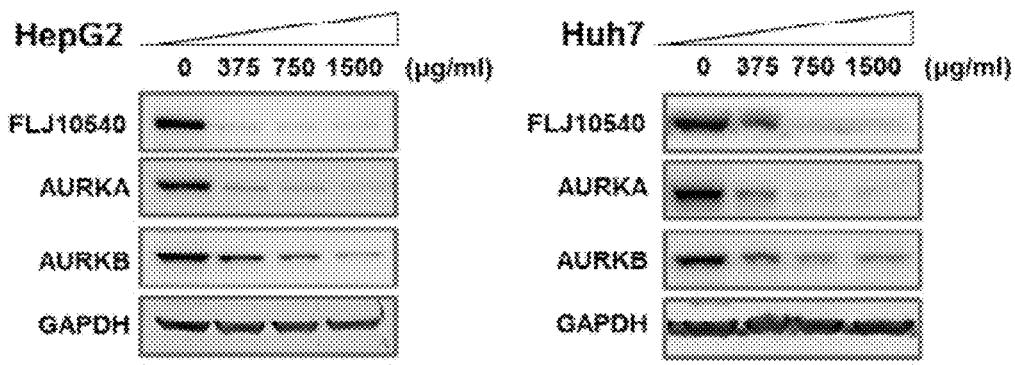
Figure 3C:
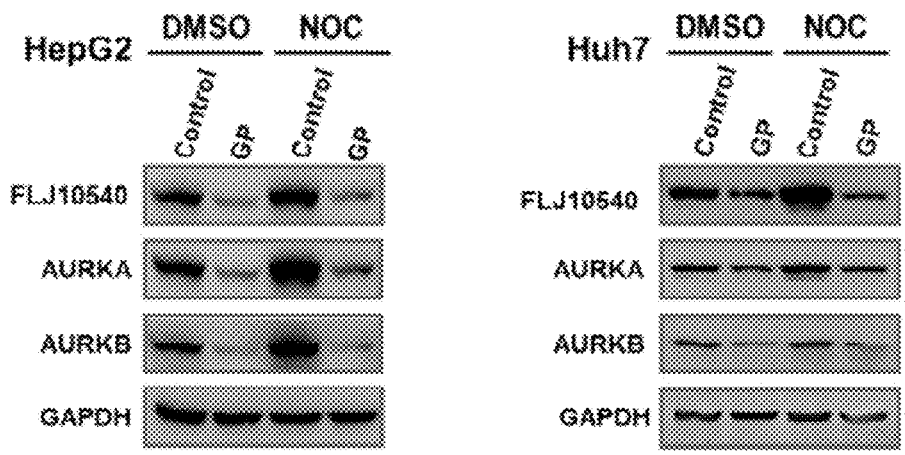

The GP Reduced AURKA, AURKB and FLJ10540 Protein Expression Levels During Both Interphase and Mitosis in Activated Hepatic Stellate Cells and HCC Cell Lines AURKA, AURKB and FLJ10540 are oncogenes and are overexpressed in HCC. Therefore, we tested whether the different preparations of GP extracts inhibit these oncoproteins in human HCC cell lines. We found that the GP extracts (obtained from 100% methanol followed by 30% DMSO extraction, as described in the methods section and referred to as 30% DMSO GP extracts) inhibited the protein expression levels of Flj10540 and Aurkb in activated hepatic stellate cells (HSC-T6) (FIG. 3A) and suppressed the protein expression levels of FLJ10540, AURKA, and AURKB in HCC cells (HepG2 and Huh7) (FIG. 3B). The expression levels of both AURKA and FLJ10540 are higher during metaphase than interphase. We next investigated whether GP inhibits the expression of these two proteins during mitosis in HCC cells. Huh7 and HepG2 cells were treated with 50-75 ng/ml nocodazole for 18 hours, followed by treatment with the 30% DMSO GP extracts for 3 hours without washing out the nocodazole. Consistent with previous findings, AURKA, AURKB, and FLJ10540 were highly expressed during mitosis. The protein expression levels of AURKA, AURKB, and FLJ10540 were decreased during both interphase and metaphase (FIG. 3C), whereas no significant changes were observed in the other mitotic proteins that we examined, including PIN1, HURP, and PLK (data not shown).

Figure 4A:
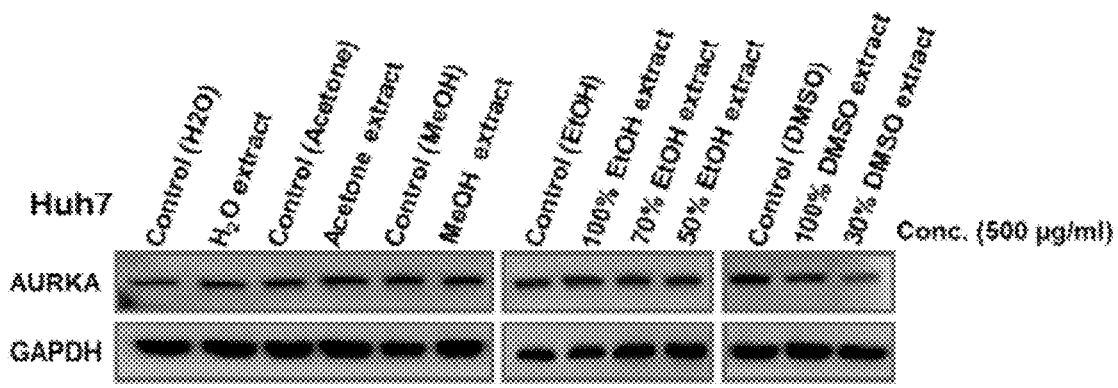
FIG. 4 shows the effects of the fraction HH-F3 according to the invention in suppressing AURKA protein expression in the HCC cell lines: Huh7 cells (A) and HepG2 and Huh7 cells (B); wherein (A) Huh7 cells were treated with GP extracts that were prepared from water, acetone, methanol, 100% ethanol, 70% ethanol, 50% ethanol, 100% DMSO, 30% DMSO at a concentration of 500 µg/ml for 48 hours; and AURKA expression levels were inhibited after treatment with the 30% DMSO GP extracts; (B) AURKA, AURKB, and FLJ10540 expression levels were not suppressed by the water and BuOH fractions in the HepG2 and Huh7 cells.
Figure 4B:
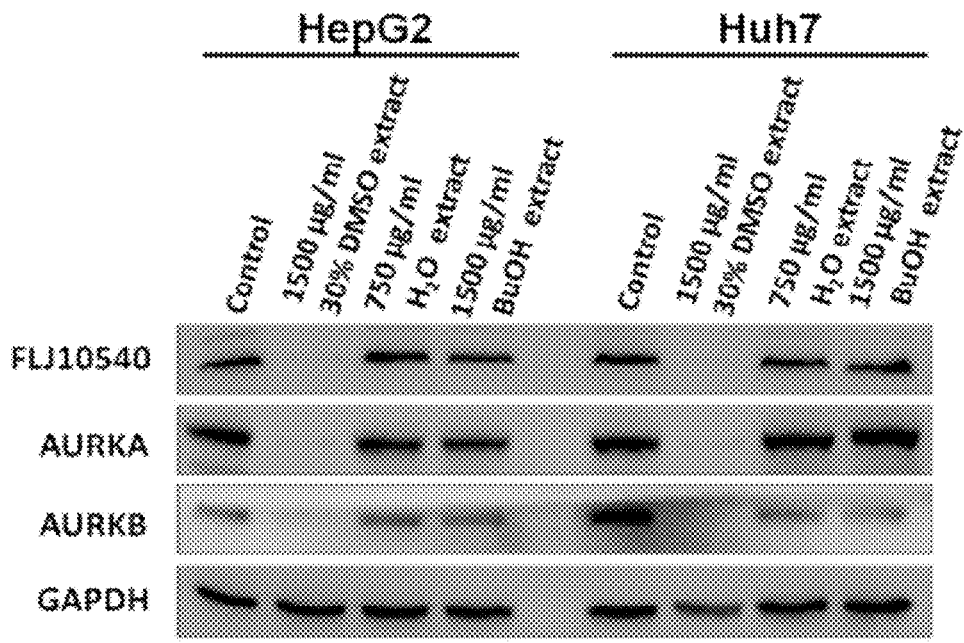
Figure 5A:
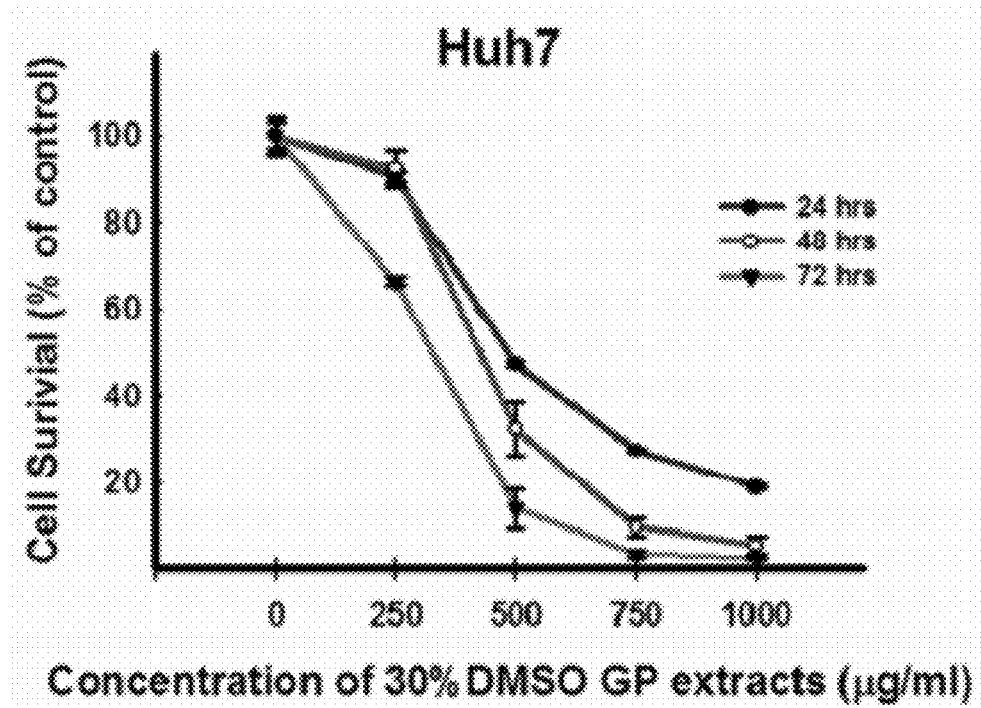
FIG. 5 shows the time- and dose-dependent response in causing cytotoxicity of the fraction HH-F3 according to the invention in the two HCC cell lines: Huh7 cells (A) and Mahlavu cells (B)1; wherein Huh7 (A) and Mahlavu (B) cells were treated with the 30% DMSO GP extracts at concentrations of 0, 250, 500, 750, and 1000 µg/ml for 24, 48, and 72 hours, followed by MTT assays. The $IC_{50}$ values for growth inhibition caused by the 30% DMSO GP extracts in Huh7 and Mahlavu cells were approximately 500 and 250 µg/ml at 48 hours, respectively.
Figure 5B:
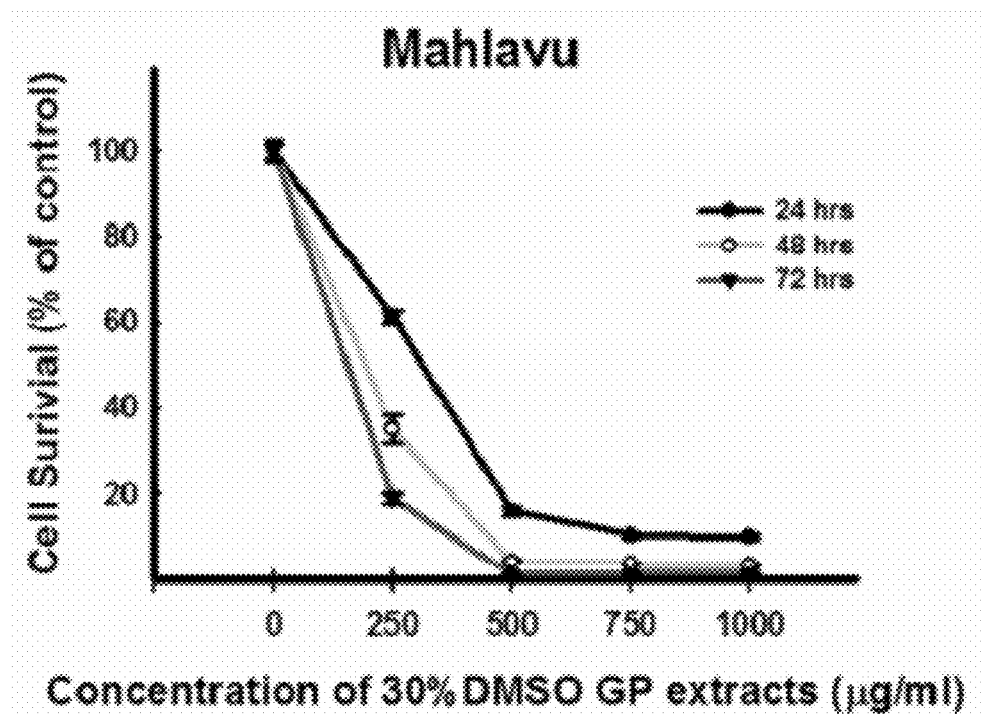

The 30% DMSO GP Extracts (the Fraction HH-F3), but not the Other Extracts that were Prepared from Different Solvent, Suppressed AURKA Protein Expression in HCC Cell Lines Human HCC Huh7 cells were treated with 500 μg/ml of the different preparations of GP extracts for 48 hours. The 30% DMSO extract significantly inhibited the protein expression levels of AURKA in these cells (FIG. 4A). In contrast, the GP extracts obtained from either water or butanol did not inhibit the protein expression levels of AURKA or AURKB in HepG2 cells after 3 hours of treatment (FIG. 4B). Because AURKA and FLJ10540 are overexpressed in HCC, we examined whether GP has an effect on the growth of HCC cells. We found that the 30% DMSO GP extracts caused cytotoxicity of Huh7 and Mahlavu cells with a 50% inhibitory concentration of cell viability ($IC_{50}$), which was determined to be approximately 500 and 250 μg/ml at 48 hours post-treatment, respectively (FIG. 5).

HH-F3 Suppressed AURKA Protein Expression in HCC Cell Lines

The 30% DMSO GP extracts reduced the protein expression levels of AURKA and FLJ10540 in activated hepatic stellate cells and hepatoma cells (FIG. 2), suggesting that we could use this assay to purify the active molecule(s) in GP. Using a Sephadex LH-20 column, we obtained four fractions from the 30% DMSO GP extracts (FIG. 6A). Only the third fraction (referred to as HH-F3) suppressed the expression of AURKA and AURKB in HepG2 cells, as examined by Western blot at 3 hours post-treatment, while the other fractions (HH-F1, HH-F2 and HH-F4) did not inhibit AURKA and AURKB protein expression (FIG. 6B). Taken together, GP extracts prepared from 30% DMSO and the HH-F3 fraction inhibited the protein expression levels of AURKA and AURKB in HepG2 cells at 3 hours post-treatment (FIGS. 6B and 6C). We further obtained an active subfraction from HH-F3, which is referred to as HH-F3a (with a yield of 71.9% compared to the amount of the starting material HH-F3), using dialysis. This HH-F3a fraction, but not HH-F3b fraction, contained the active compounds, as determined by measuring the disappearance of AURKA by Western blot (FIG. 6D).

Figure 7A:
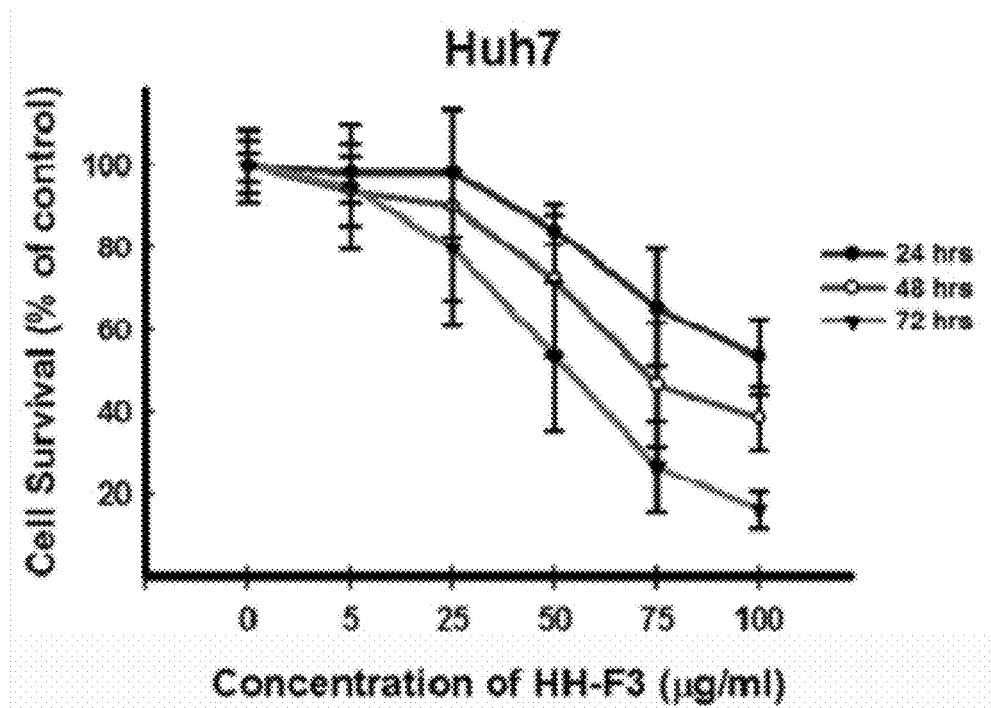
FIG. 7 shows the effects of the fraction HH-F3 according to the invention in inhibition of the cell viability of Huh7 cells (A, E), Mahlavu cells (B, F), PLC5 cells (C, G) and HSC-T6 cells (D); wherein Huh7 (A, E), Mahlavu (B, F), PLC5 (C, G) and HSC-T6 (D) cells were treated with the HH-F3 fraction at concentrations of 5, 25, 50, and 75 µg/ml for 24, 48, and 72 hours, followed by MTT assays (A-D) and trypan blue assays (E-F). The $IC_{50}$ values for the inhibition of cell viability caused by treatment with the HH-F3 fraction in, Huh7, Mahlavu, PLC5, and HSC-T6 cells were approximately 50, 37.5, 75, and 20 μg/ml, respectively, after treatment for 72 hours.
Figure 7B:
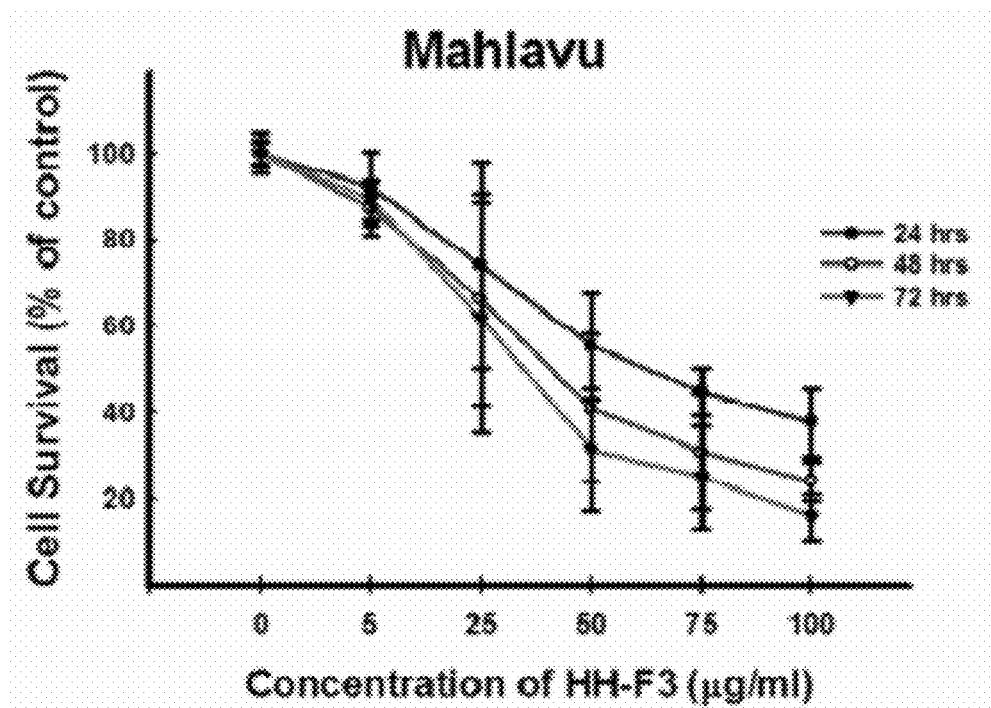
Figure 7C:
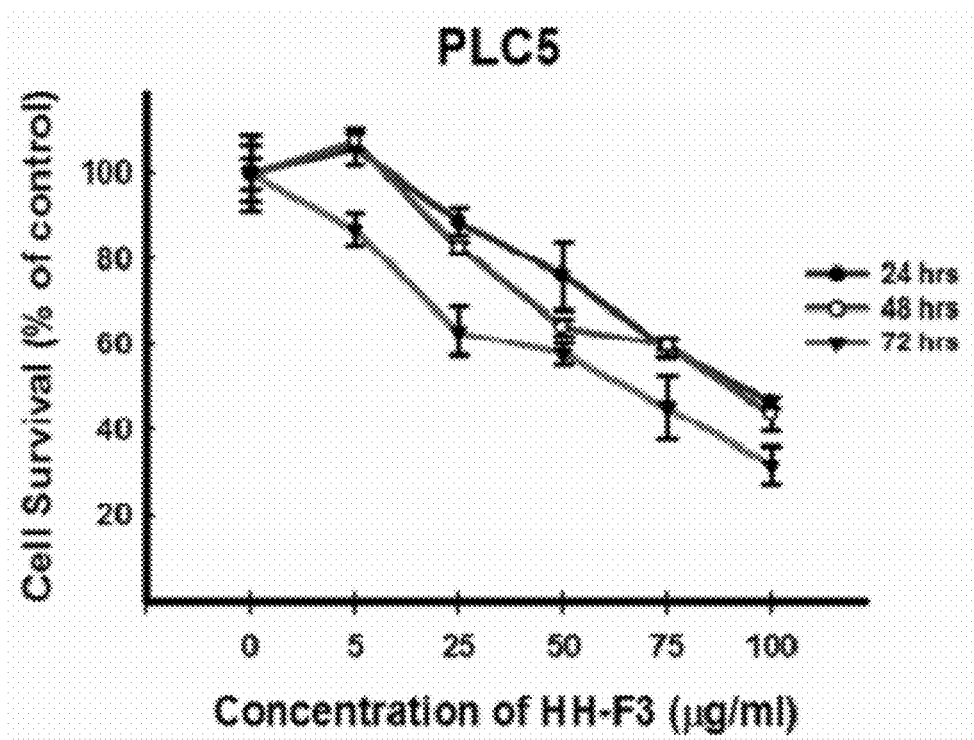
Figure 7D:
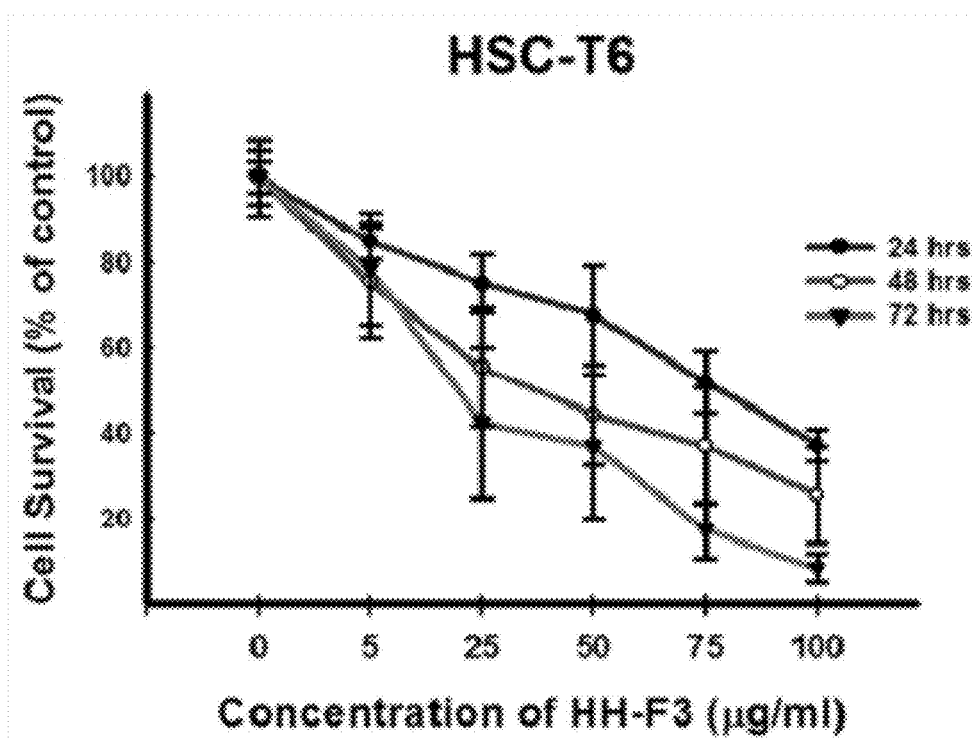
Figure 7E:
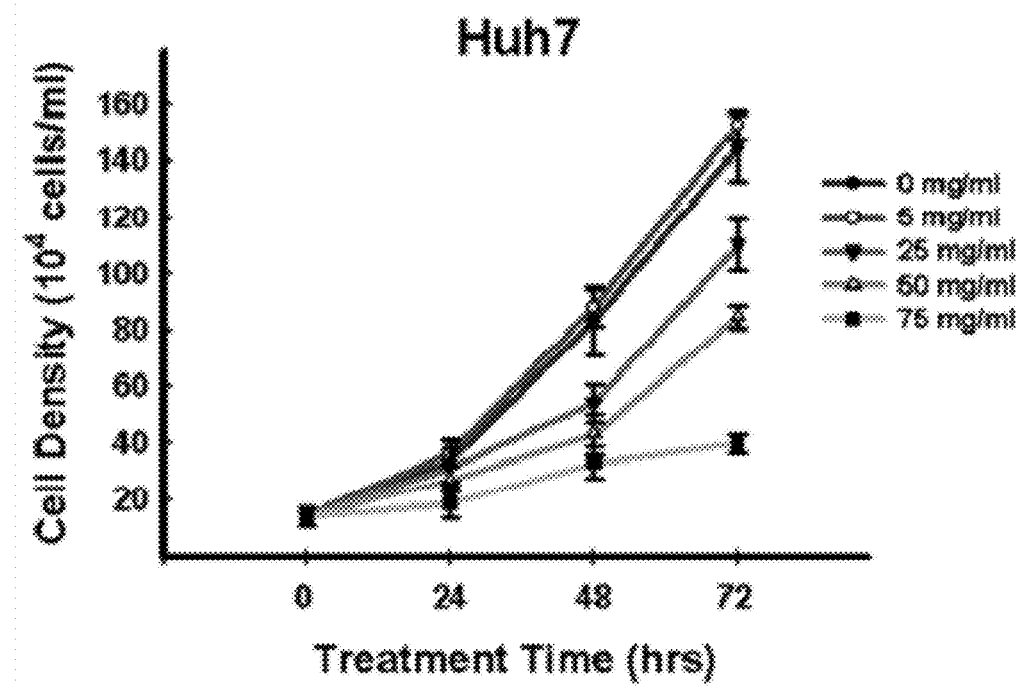
Figure 7F:
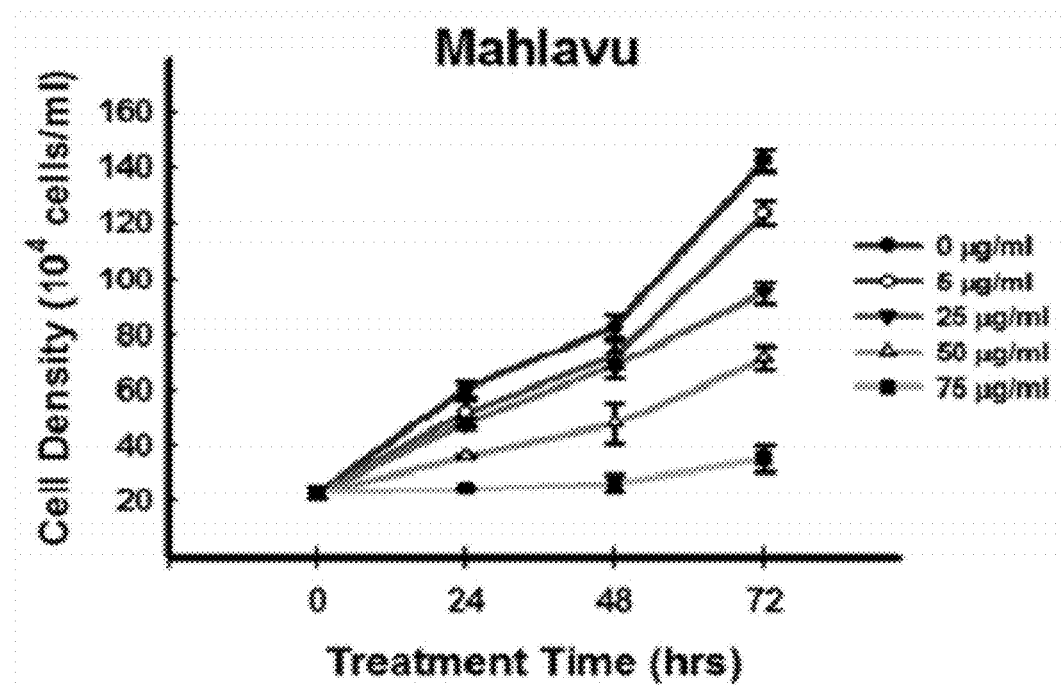
Figure 7G:
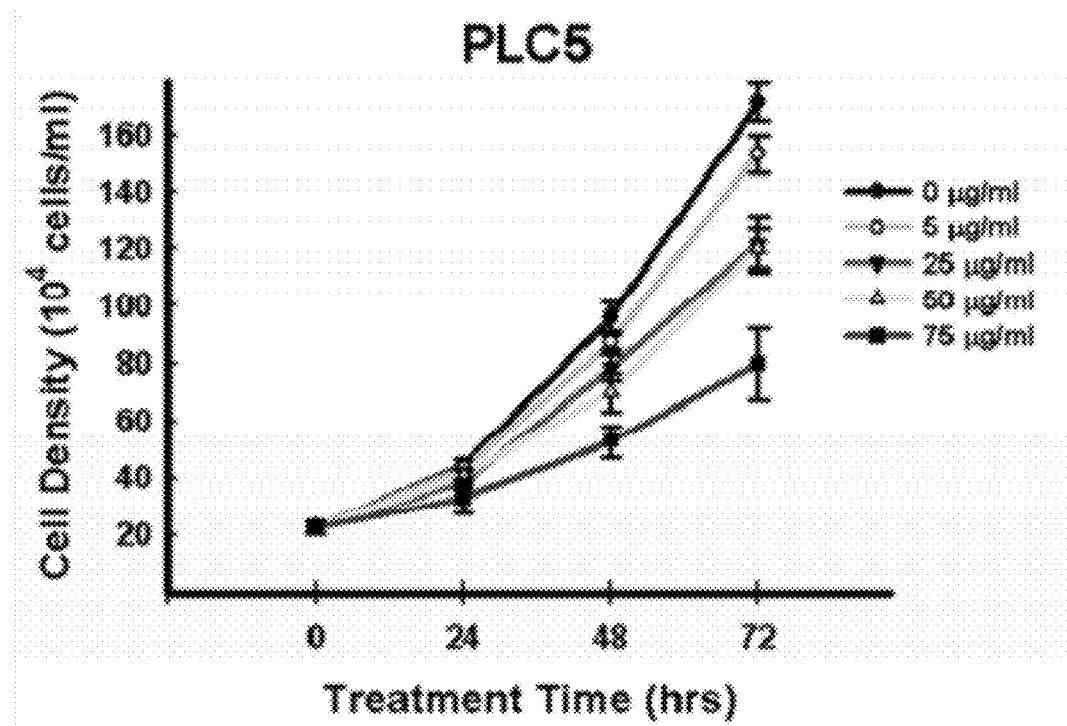

The HH-F3 fraction reduces cell viability in HSC-T6 cells and HCC cell lines To investigate the effects of the HH-F3 fraction on cell viability, Huh7, Mahlavu, PLC5, and HSC-T6 cells were treated with the HH-F3 fraction at concentrations of 5, 25, 50, 75, and 100 μg/ml for 24, 48, and 72 hours. The survival of these tested cell types were inhibited in response to HH-F3 treatment, as examined by the MTT assay. The $IC_{50}$ values for treatment with the HH-F3 fraction in Huh7, Mahlavu, PLC5, and HSC-T6 cells at 72 hours were approximately 50, 37.5, 75, and 20 μg/ml, respectively (FIGS. 7A-7D). To further confirm this finding, cell survival was determined by trypan blue staining of Huh7, Mahlavu, and PLC5 cells. Decreases in cell survival after treatment with the HH-F3 fraction were demonstrated in a time- and dose-dependent manner after 24, 48, and 72 hours at concentrations of 5, 25, 50, 75, and 100 μg/ml (FIG. 7E-7G). Taken together, both the 30% DMSO GP extracts and the HH-F3 fraction can inhibit the cell viability of HCC cell lines and activated hepatic stellate cells.

Figure 8A:
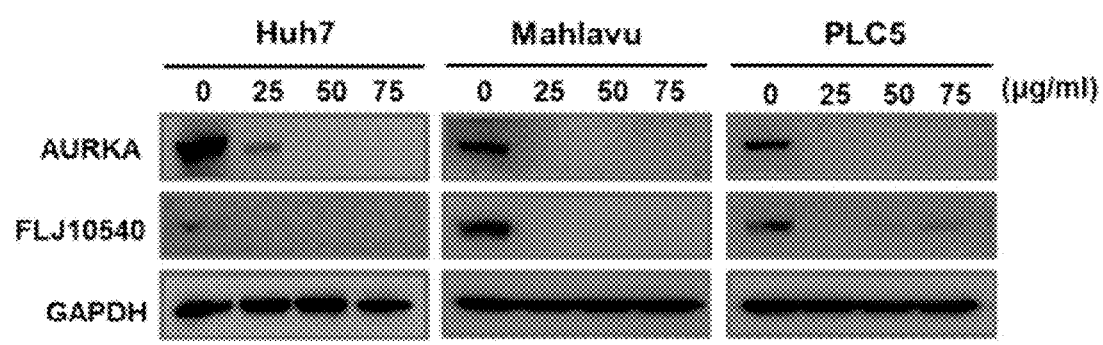
FIG. 8(A) shows that Huh7, Mahlavu, and PLC5 cells were treated with the HH-F3 fraction at concentrations of 25, 50, or 75 μg/ml for 3 hours. Expression of both AURKA and FLJ10540 was down-regulated in a concentration-dependant manner, as examined by immunoblot analysis with anti-FLJ10540 and anti-AURKA antibodies.
Figure 8B:
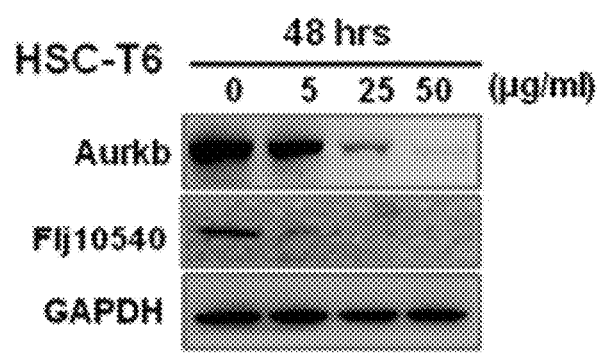
FIG. 8(B) shows that HSC-T6 cells were treated with the HH-F3 fraction at concentrations of 5, 15, and 50 μg/ml for 3 hours; FLJ10540 expression was down-regulated in a concentration-dependant manner.

Next, Huh7, Mahlavu, PLC5, and HSC-T6 cells were treated with 25, 50, and 75 μg/ml of the HH-F3 fraction for 3 hours. The HH-F3 fraction suppressed the expression of both AURKA and FLJ10540 in all three tested HCC cell lines and HSC-T6 cells (FIGS. 8A and 8B). To investigate whether the inhibitory effects of the HH-F3 fraction occurred at the transcriptional level, we examined the variation in the gene expression levels of FLJ10540 and the Aurora kinase family (AURKA, AURKB, and AURKC). HepG2 cells were treated with 50 µg/ml of the HH-F3 fraction for 6 hours, after which gene expression levels were analyzed by microarray (U133A chip, Affymetrix), and protein levels were analyzed by Western blot. Compared with the control group, there was no change in the gene expression levels of the specific genes mentioned above after treatment with the HH-F3 fraction (data not shown), despite a decrease in protein levels. Therefore, the HH-F3 fraction probably regulates HCC cell growth at the protein level and not at the transcriptional level.

The HH-F3 Fraction Leads to Cell Death Via Apoptosis in HCC Cell Lines

Figure 9A:
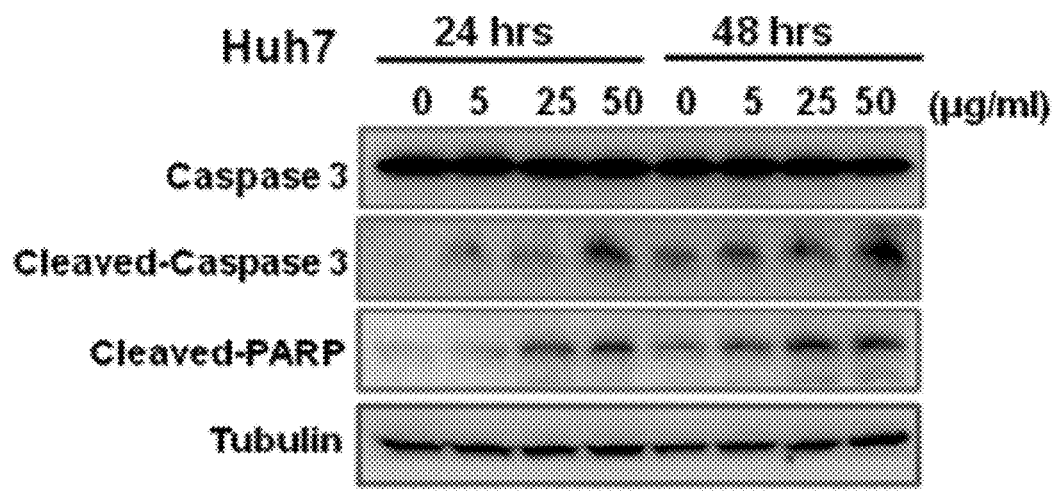
FIG. 9(A) shows the results of Huh7 cells and FIG. 9(B) shows the results of Mahlavu cells.
Figure 9B:
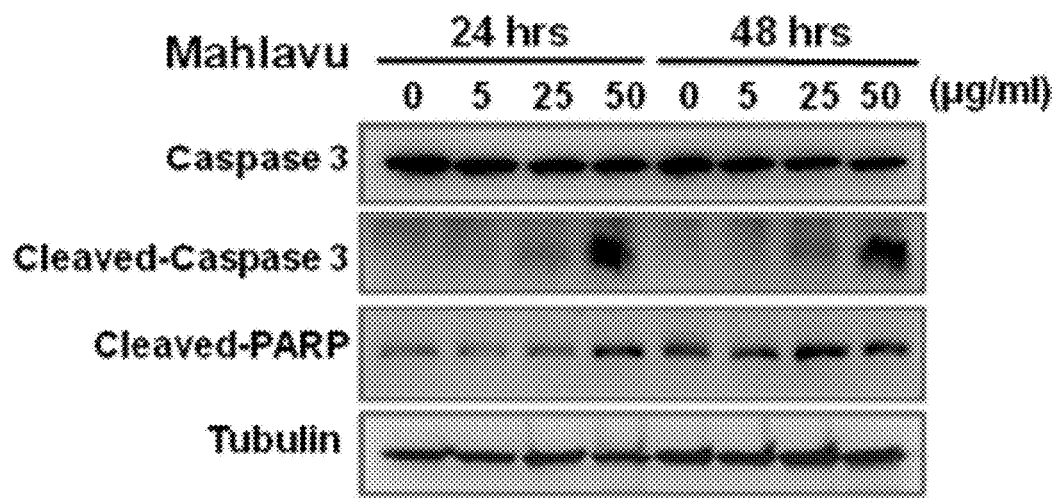

The extracts were analyzed for the effects of the HH-F3 fraction on the cell cycle profiles of HCC cells using propidium iodide (PI) staining Huh7 and Mahlavu cells were treated with 5, 25, and 50 µg/ml HH-F3 for 48 hours. The HH-F3 fraction disturbed the cell cycle progression of Huh7 and Mahlavu cells. After 48 hours of treatment with 50 µg/ml of the HH-F3 fraction, the sub-G1 population of Huh7 was 22%, while it was 26% in Mahlavu cells. The HH-F3 fraction generated a larger increase in the sub-G1 population in Mahlavu cells than in Huh7 cells, which is in accordance with the cytotoxic effects demonstrated earlier (data not shown). We next examined the ability of the HH-F3 fraction to induce apoptotic cell death in Huh7 and Mahlavu cells. The protein expression levels of cleaved caspase-3 and cleaved PARD were increased in a dose-dependent manner at concentrations of 5, 25, and 50 µg/ml for 24 and 48 hours. Under the same concentration, HH-F3 fraction also resulted in the up-regulation of apoptotic molecule FAS and the down-regulation of BCL2 and BCL-XL (data not shown). These data indicate that the HH-F3 induces caspase-dependent apoptotic cell death (FIGS. 9A and 9B).

Figure 10A:
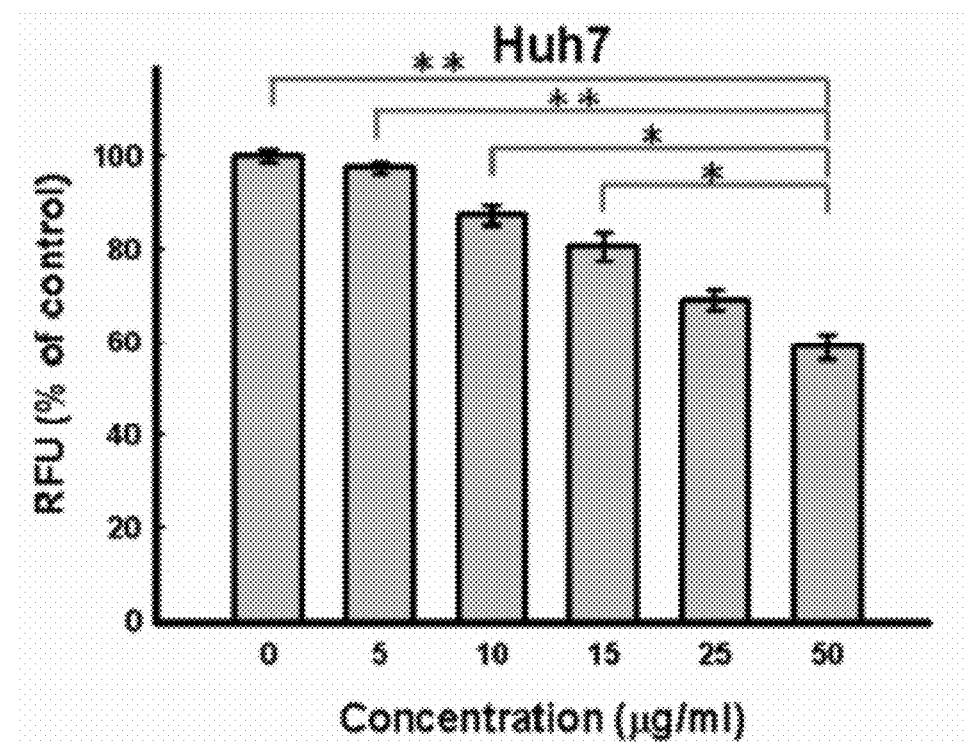
FIG. 10(A) and FIG. 10(B) show that Mitochondria membrane potential ($\Delta\Psi$) of Huh7 and Mahlavu cells was analyzed using the JC-1 mitochondrial membrane potential assay, and the $\Delta\Psi$ of the cells decreased after treatment with the fraction HH-F3 at the concentrations of 5, 10, 15, 25, and 50 μg/ml for 48 hours (n=2); RFU=$\Delta\Psi$.
Figure 10B:
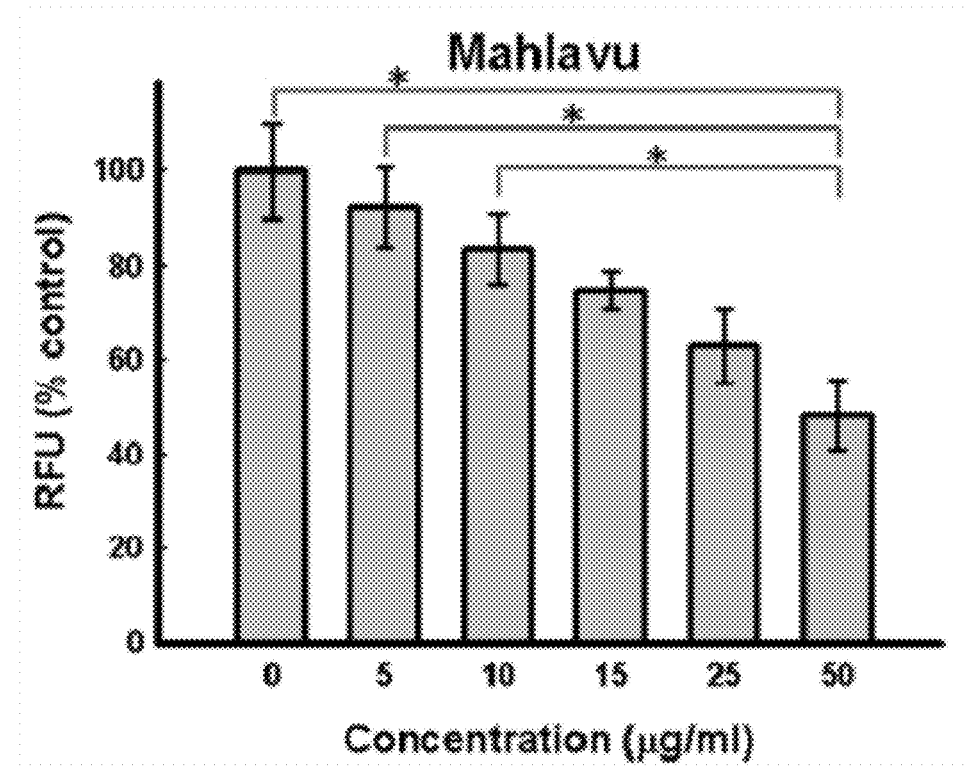

The HH-F3 Fraction Decreases Mitochondrial Membrane Potential and Increases ROS in HCC Cell Lines Reactive oxygen species (ROS) and mitochondria play an important role in apoptosis induction under both physiological and pathological conditions. We next investigated whether the HH-F3 fraction triggers apoptosis via the extrinsic or intrinsic pathway. We tested whether mitochondrial membrane potential, one of the indicators of the intrinsic pathway, might be altered in HCC cells. Huh7 and Mahlavu cells were treated with 5, 25, and 50 µg/ml of the HH-F3 fraction, and the mitochondrial membrane potential of the cells was examined after 48 hours of treatment. Compared to the control group, the number of apoptotic cells was increased. This is in agreement with mitochondrial membrane potential ($\Delta\Psi$) results, which show that the membrane potentials were decreased in Huh7 and Mahlavu cells after treatment with the HH-F3 fraction (FIG. 10A).

Figure 10C:
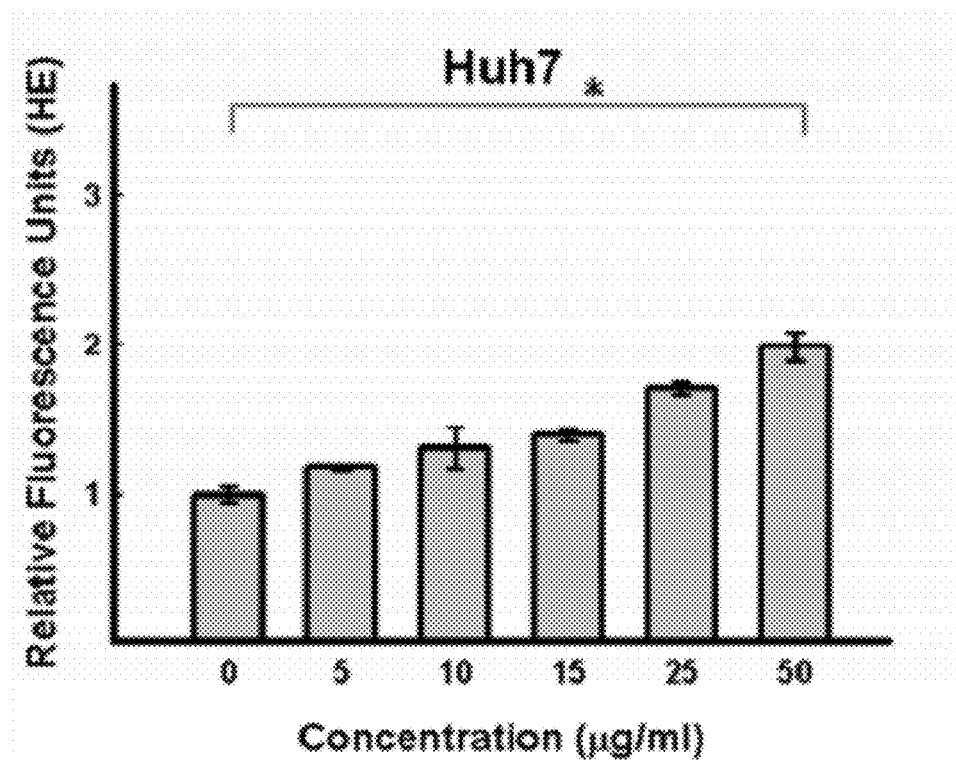
FIGS. 10(C) and 10(D) show that intracellular superoxide ($O_2^-$) levels, as measured by hydroethidine (HE) staining, were decreased significantly 48 hours after treatment with the fraction HH-F3 at the concentrations of 5, 10, 15, 25, and 50 μg/ml as compared with the control HCC cells (Huh7 and Mahlavu cells treated with DMSO)
Figure 10D:
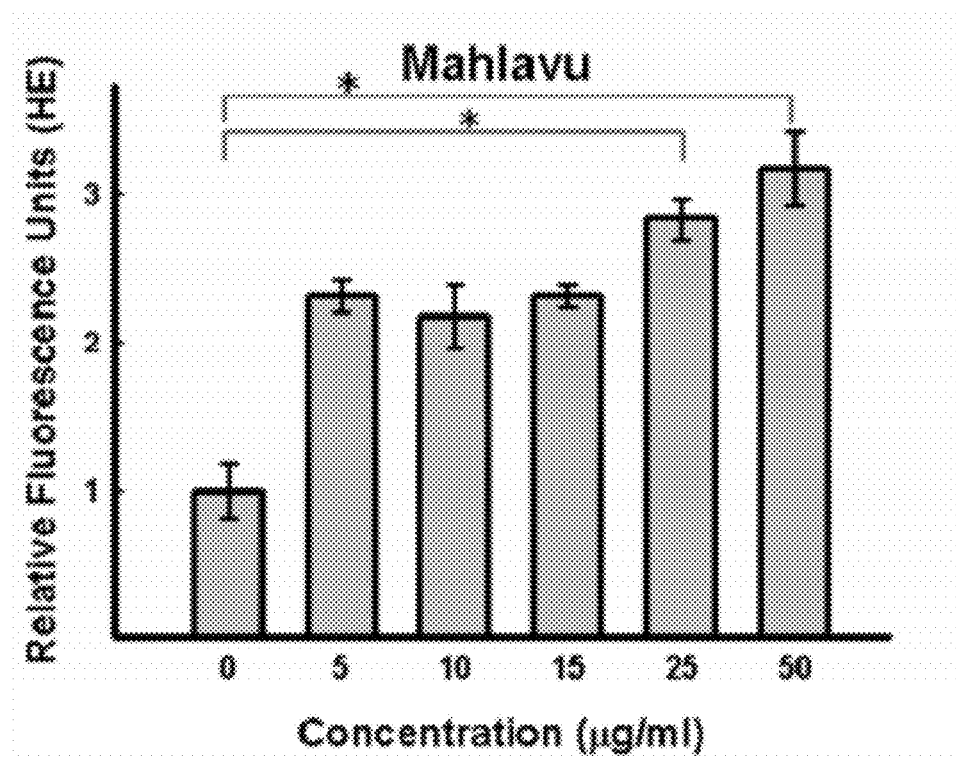
Figure 10E:
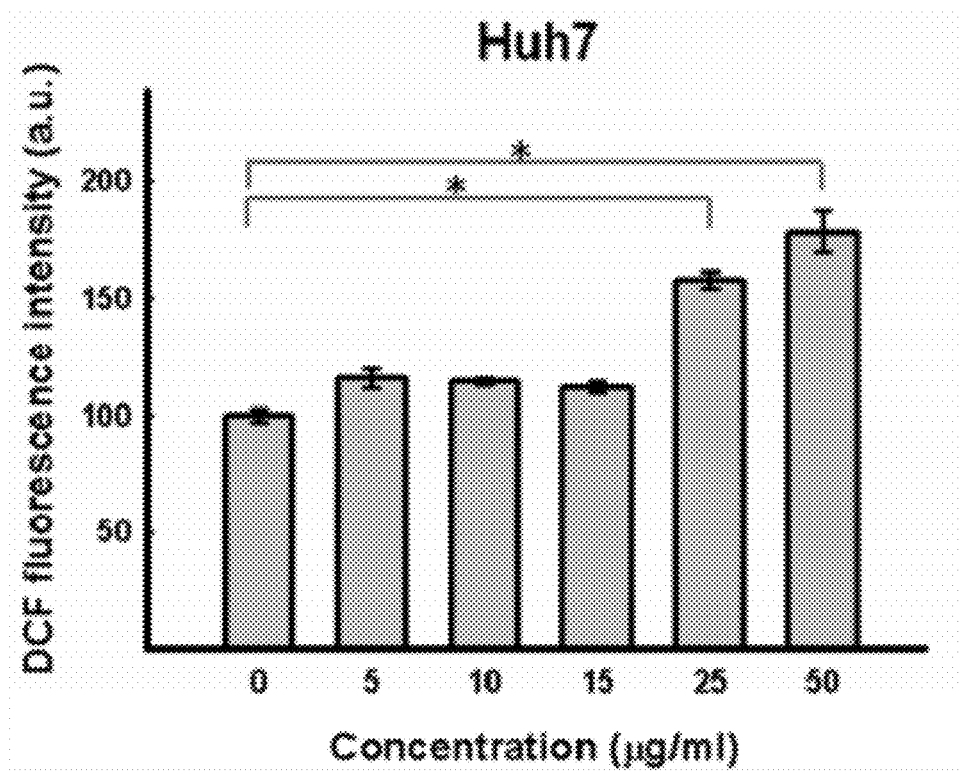
FIG. 10(E) and FIG. 10(F) show that intracellular peroxide levels, as measured by DCFH, were increased 48 hours after treatment with the fraction HH-F3 at the concentrations of 5, 10, 15, 25, and 50 μg/ml as compared with control HCC cells (Huh7 and Mahlavu treated with DMSO), and it was found that the production of intracellular peroxide and superoxide increased in a dose-dependent manner in Huh7 and Mahlavu cells after treatment with the fraction HH-F3.
Figure 10F:
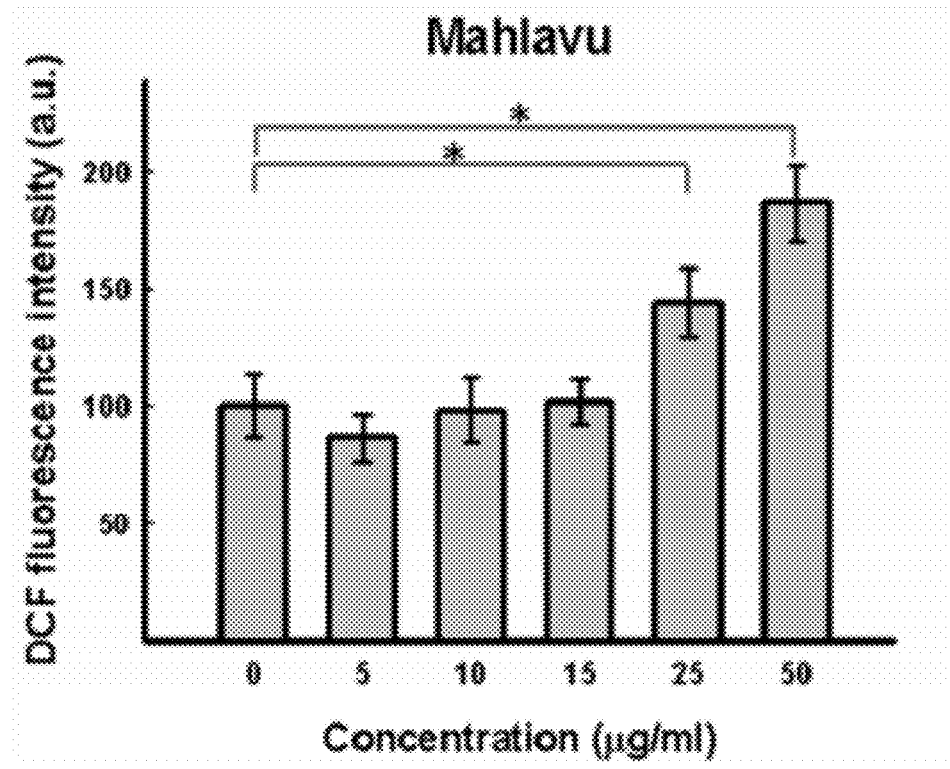

Several reports have shown that ROS are generated only after the loss of $\Delta\Psi$. ROS include superoxide anions, hydrogen peroxide, and hydroxyl radicals, all of which are derived from oxygen. ROS are produced as a consequence of electron transport processes during photosynthesis and aerobic respiration. ROS, at the physiological concentrations required for normal cellular function, are involved in intracellular signaling and redox regulation. Excessive levels of ROS cause oxidative stress, which is potentially harmful to cells because it causes the oxidation of lipids, proteins and DNA. We tested whether stimulation of the HCC cells with the HH-F3 fraction would result in changes in the production of ROS. Intracellular generation of $O_2^-$ was assessed by hydroethidine fluorescence, and the level of intracellular peroxide was determined with DCFH diacetate. After the cells were treated with the HH-F3 fraction, cellular production of intracellular peroxide (FIGS. 10C and 10D) and superoxide (FIGS. 10E and 10F) were increased in HCC cells. This suggests that the HH-F3 fraction causes apoptosis via the intrinsic pathway.

Figure 11:
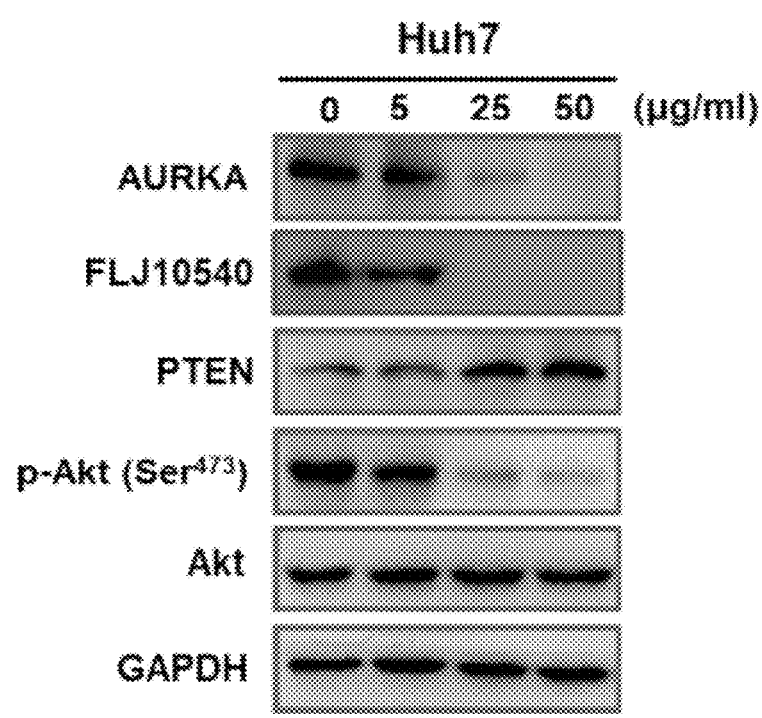
FIG. 11 shows the effect of the fraction HH-F3 in inhibiting AKT-Ser$^{473}$ phosphorylation and activating PTEN protein expression in Huh7 cells that were treated with the fraction HH-F3 at the concentrations of 25, 50, or 75 μg/ml for 48 hours, and the expression of AURKA, FLJ10540, AKT-Ser$^{473}$ was down-regulated, whereas PTEN was up-regulated in a concentration-dependant manner, as examined by immunoblot analysis with anti-FLJ10540, anti-AURKA, anti-AKT-Ser$^{473}$, and anti-PTEN antibodies.

The HH-F3 Fraction Decreased the Phosphorylation of Akt and Enhances the Expression of PTEN Some cell proliferation pathways are related to apoptosis inhibition and abnormality in HCC, for example AKT pathway. Because HH-F3 caused cell cytotoxicity on HCC cells, we then investigated whether HH-F3 affected the cell proliferation pathways on HCC cells. The Huh7 cells were treated with HH-F3 at 5, 25, 50 µg/ml for 48 hours, respectively. In Huh7 cells, the $Ser^{473}$ phosphorylation of AKT was down-regulated under HH-F3 treatment, whereas the total AKT protein was not influenced (FIG. 11). Interestingly, HH-F3 activated the protein level of phosphatase and tensin homolog (PTEN), which is a negative regulator of PI3K/AKT dependent signaling. These results indicated that HH-F3 may modulate AKT signaling transduction pathway of cell proliferation to induce cell apoptosis.

GP Extracts Increased Bile Excretion Function of Cirrhotic Animals

Figure 12A:
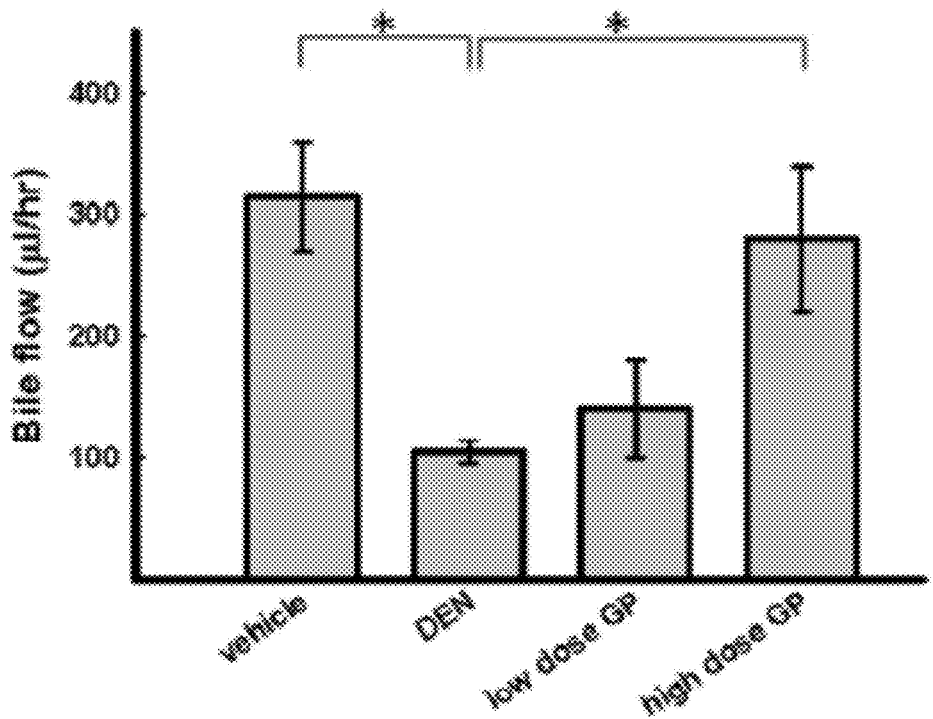
FIG. 12(A) shows the decreased bile flow in cirrhotic animals, which was recorded to measure liver function ($*P<0.05$; ANOVA)
Figure 12B:
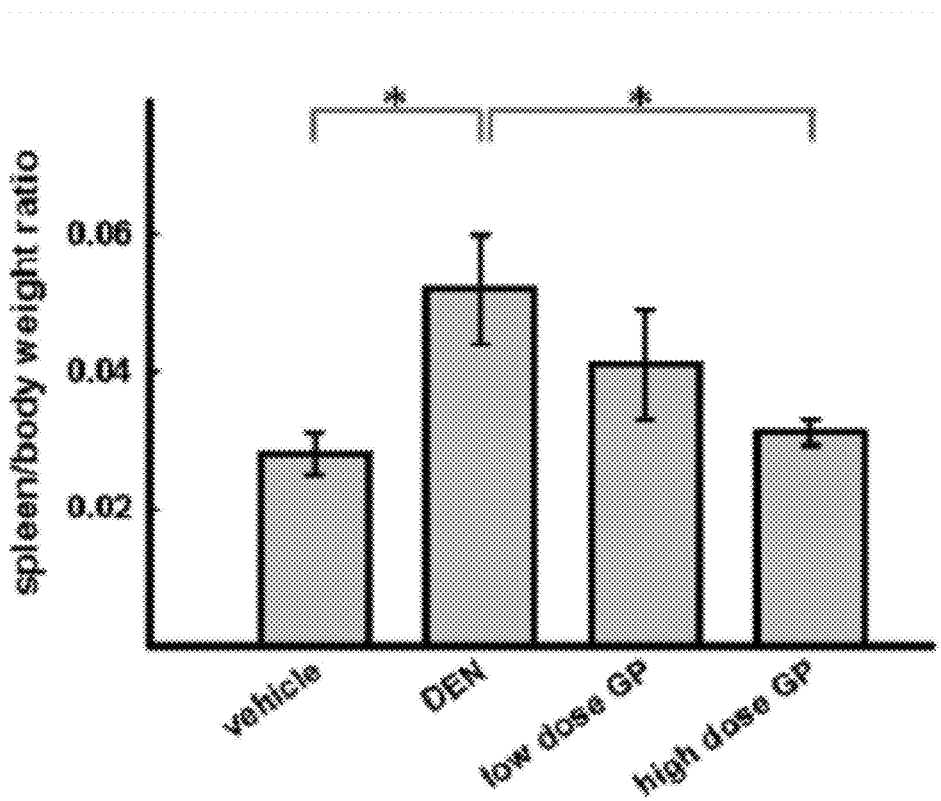
FIG. 12(B) shows the enlarged spleen size in cirrhotic animals wherein the spleen weights and body weights (BWs) were measured and expressed as spleen weight/BW; the ratios of spleen weight/BW of the DEN group was significantly higher than those of the normal group, which indicates that the splenomegaly was due to cirrhosis-related portal hypertension ($P<0.05$, ANOVA), whereas only the ratio of spleen weight/BW of the high-dose group was significantly lower than those of the DEN group ($P<0.05$, ANOVA)
Figure 12C:
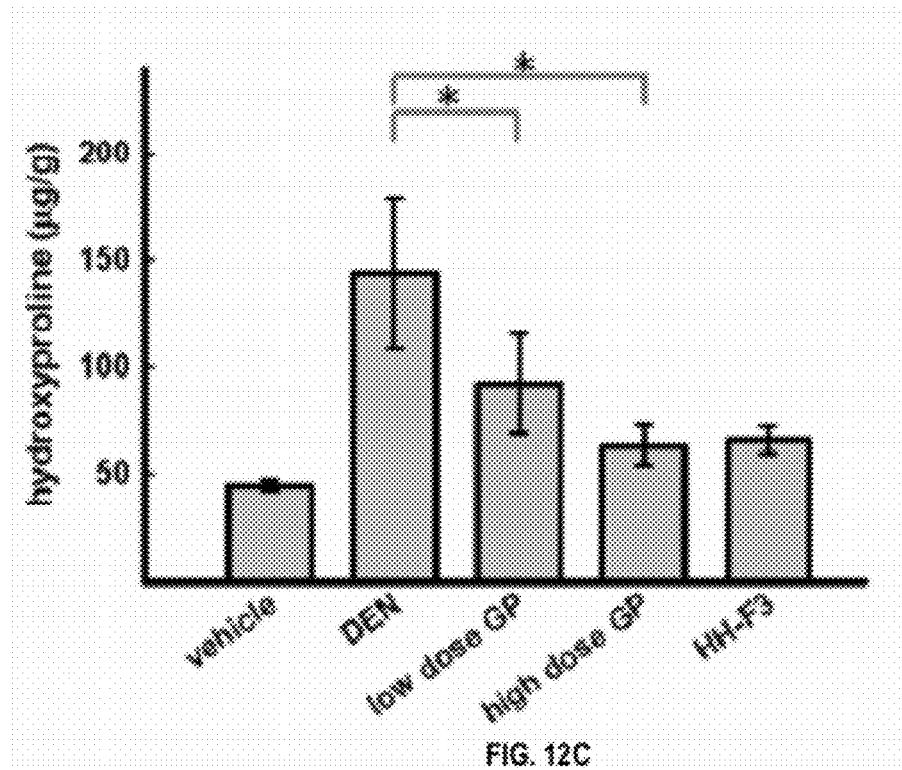
FIG. 12(C) shows the increased collagen content in cirrhotic livers, wherein liver cirrhosis was determined by measuring the levels of liver hydroxyproline content and significant decreases were observed when comparing the high-dose group, the HH-F3 group and the control group.
Figure 12D:
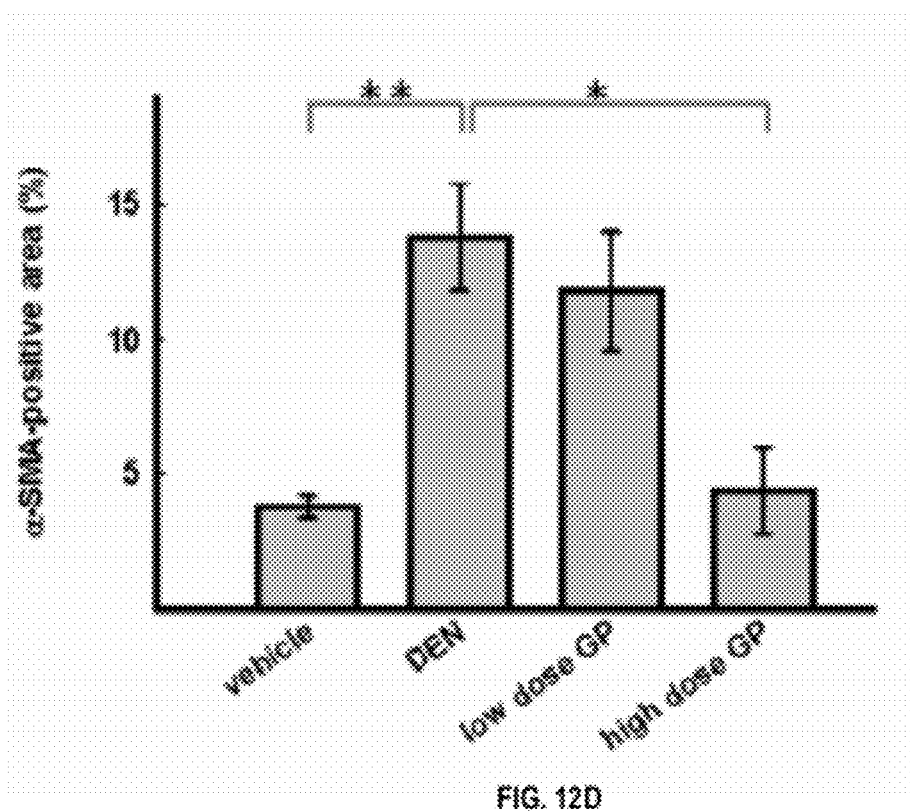
FIG. 12(D) shows the expression of $\alpha$-SMA induced by DEN. The formalin/paraffin sections of the liver samples from each group during the course of DEN feeding stained with an antibody against $\alpha$-SMA, the percentages of $\alpha$-SMA (+) area were determined by a Digital Camera System using the 10 fields with the densest staining ($*P<0.05$; $P<0.005$, ANOVA)

Liver cirrhosis was also evaluated by measuring bile flow rates, reflecting liver function (FIG. 12A), by quantifying the ratios of spleen weight/body weight, an indicator due to cirrhosis-related portal hypertension (FIG. 12B), and by analyzing the expression of α-SMA induced by DEN (FIG. 12D). All of the data demonstrated that the status of liver cirrhosis was improved after treated by high-dose GP, and presented as increasing bile flow, decreased spleen size and decreased the percentages of α-SMA (+) area significantly.

GP Extracts and HH-F3 Decrease the Hydroxyproline Content in Cirrhotic Liver

Liver fibrosis was determined by measuring the levels of liver hydroxyproline content. Significant increases of hydroxyproline level were observed in DEN-induced animals (143±30 µg/g). In contrast, following treatment with low dose GP, high dose GP or HH-F3, the hydroxyproline contents were 98±18 µg/g ($P<0.05$ compared with the DEN group), 70±10 µg/g ($P<0.05$), and 72±8.2 µg/g ($P<0.05$), respectively (FIG. 12C).

GP Extracts and HH-F3 Decreased Oxidative Stress

Figure 12E:
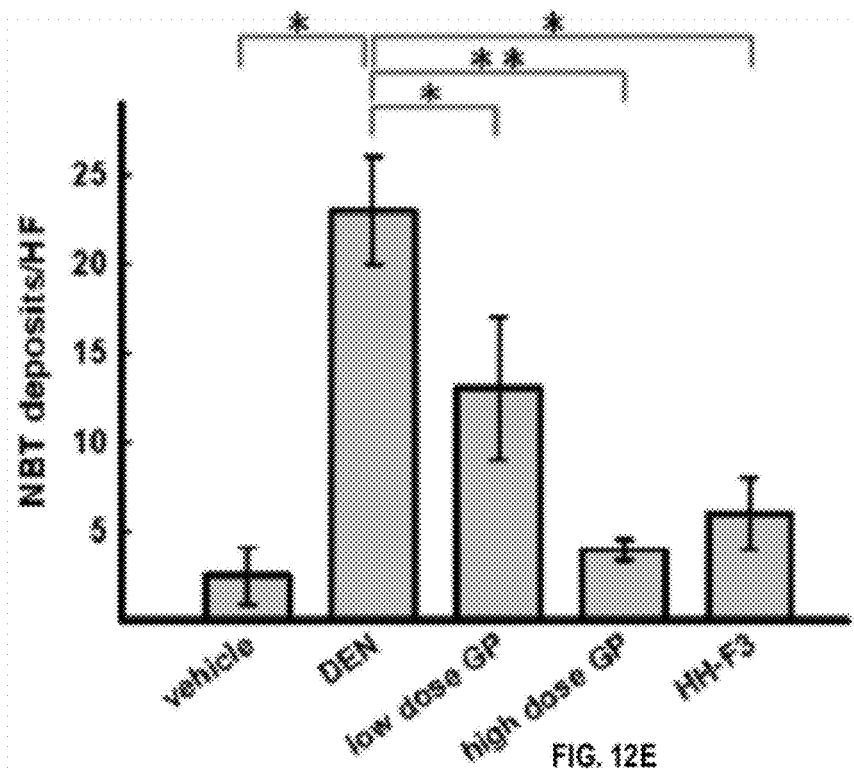
FIG. 12(E) shows the oxidative stress induced by DEN. NBT (Nitrotetrazolium blue chloride) is a dye that is reduced to an insoluble blue-colored formazan derivative upon exposure to superoxide, and the blue-colored deposit as a histological marker for the presence of superoxide in tissue is detectable by light microscopy, the density of NBT (+) foci was determined, as described in the Materials and Methods, from the 10 fields with the densest staining.

NBT (Nitrotetrazolium blue chloride) is a dye that is reduced to an insoluble blue-colored formazan derivative upon exposure to superoxide, and the blue-colored deposit as a histological marker for the presence of superoxide in tissue is detectable by light microscopy. The density of NBT (+) foci was determined from the 10 fields with the densest staining Significant increases of NBT (+) foci were observed in DEN-induced animals (23±3). In contrast, following treatment with low dose GP, high dose GP or HH-F3, the density of NBT (+) foci were 13±4 ($P<0.05$ compared with the DEN group), 4.2±0.6 ($P<0.005$), and 6.2±2.1 ($P<0.05$), respectively (FIG. 12E). These findings suggest that the oxidative stress induced by DEN could be reduced by the treatment of GP extracts and HH-F3.

GP Extracts and HH-F3 Decreased the Tumor Burdens

Figure 12F:
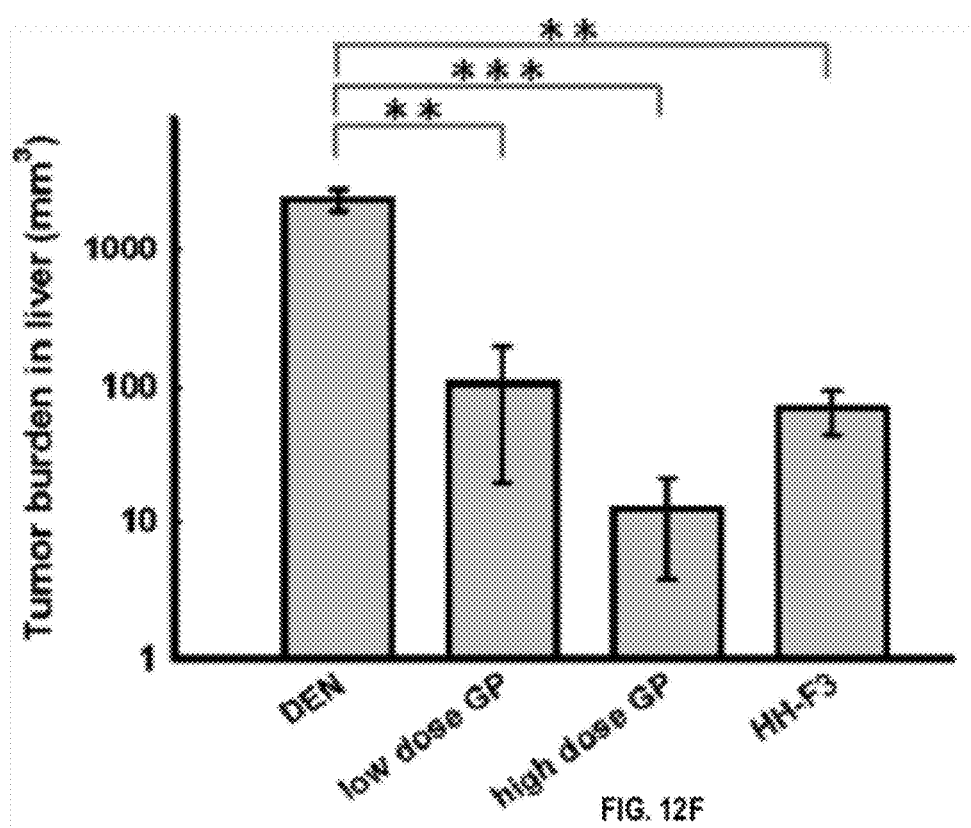
FIG. 12(F) shows the measurement of tumor burdens wherein the livers obtained from the sacrificed animals were sliced into 5-mm sections, the numbers and sizes of all visible tumor nodules with diameters larger than 3 mm were counted and measured. Tumor burdens are expressed as the sum of the volume of total tumor nodules ($P<0.005$, $***P<0.001$ as compared to the DEN group); and Figure (G) shows the gross picture of chemical-induced HCC and cirrhosis, wherein the 9 weeks of oral administration of DEN in drinking water on the rat livers resulted in multiple hepatic tumors in the cirrhotic rat livers, and the development of granulation on the surface and the uneven boundary with multiple hepatic tumors was observed in these animals.
Figure 12G:
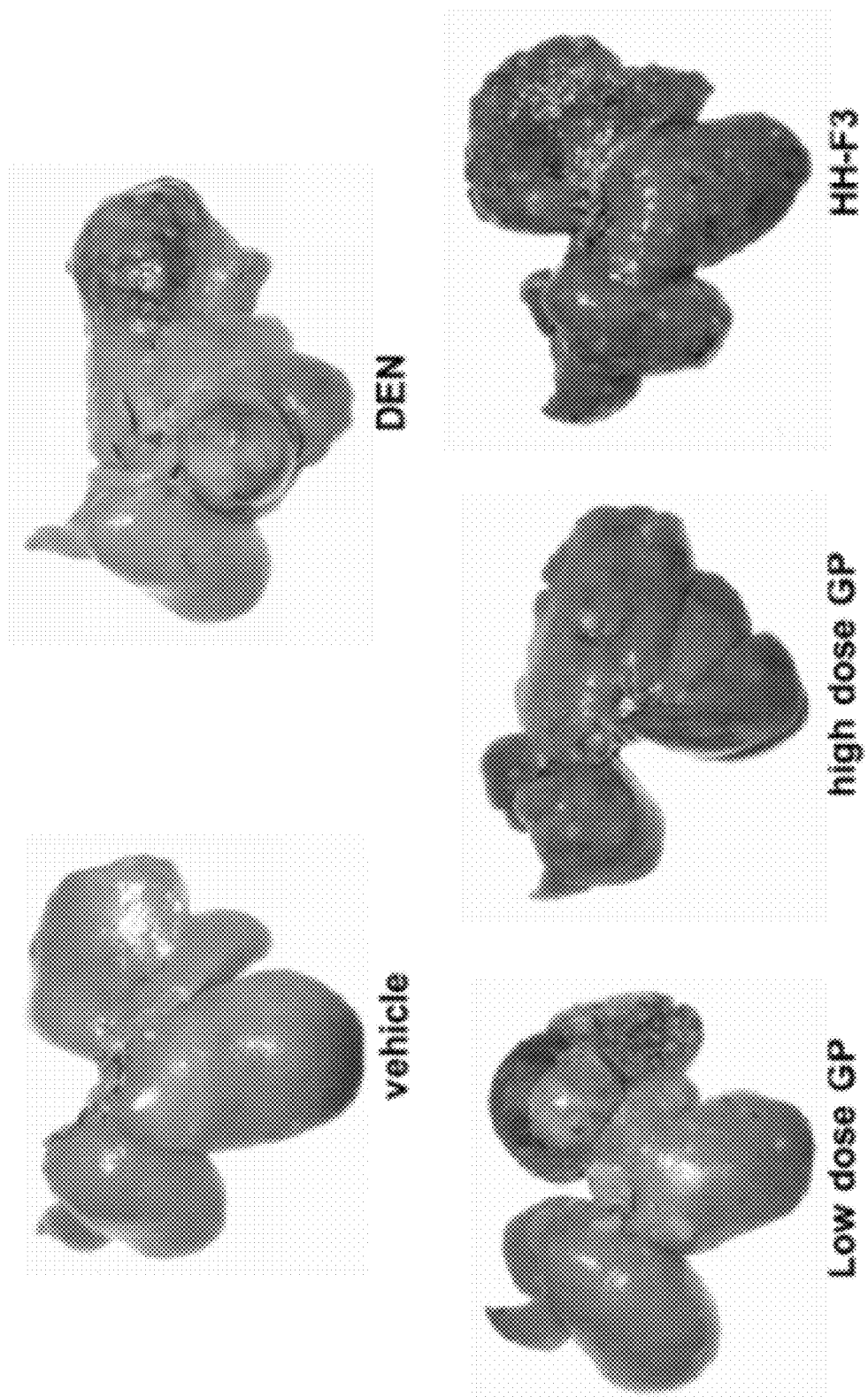
FIG. 12 shows the effects of the GP extract and the fraction HH-F3 according to the invention in decreasing the hydroxyproline content in cirrhotic liver and tumor burdens; wherein the animals were divided into four groups; they were provided with tap water only (normal group) or with DEN solution (the other group), as described in the Materials and Methods.

The livers obtained from the sacrificed animals were sliced into 5-mm sections. The numbers and sizes of all visible tumor nodules with diameters larger than 3 mm were counted and measured. Tumor burdens are expressed as the sum of the volume of total tumor nodules. Visible tumors were observed in DEN-induced animals (tumor burden 2350±905 mm$^3$. In contrast, following treatment with low dose GP, high dose GP or HH-F3, the tumor burden in liver were 110±105 mm$^3$ ($P<0.005$ compared with the DEN group), 23±31 mm$^3$ ($P<0.005$), and 86±12 ($P<0.05$), respectively (FIG. 12F). Representative photographs of the livers showed multiple hepatic tumors in the cirrhotic rat livers. The development of granulation on the surface and the uneven boundary with multiple hepatic tumors was observed in these animals, and the visible tumor number and uneven liver surface were improved after treatment of low dose GP, high dose GP or HH-F3.

Figure 13A:
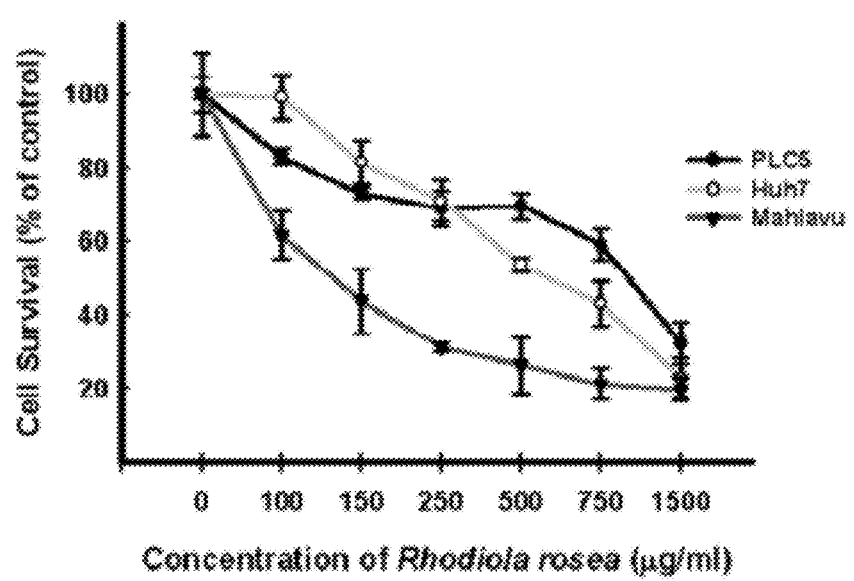
FIG. 13 shows the effect of the *Rhodiola rosea* extract in inhibiting the cell viability of the HCC cell lines and down-regulating AURKA protein expression.
Figure 13B:
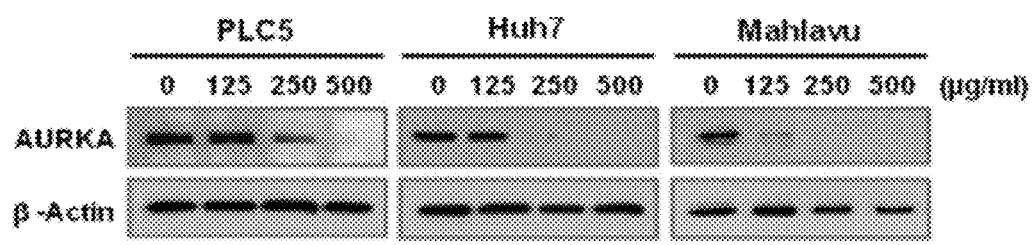

The *Rhodiola rosea* extracts were also tests and it was found that they inhibited cell viability of the HCC cell lines and down-regulate AURKA protein expression (FIG. 13).

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A compound, having a structure of formula I

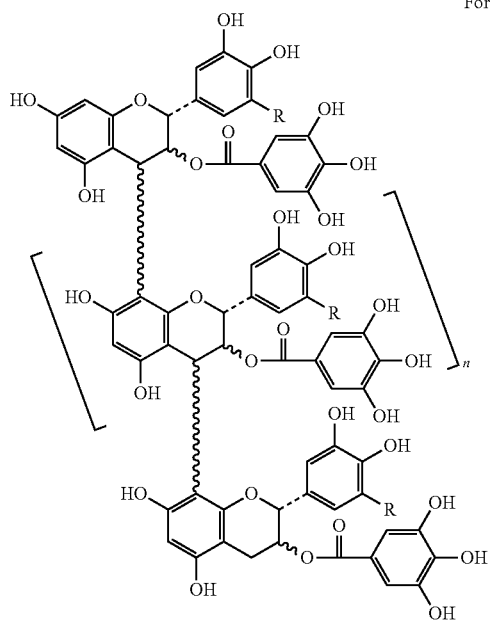

Formula I wherein one of the R's is H, or prucyanidin (PC) unit, and the other are OH or prodelphindine (PD) unit; n is a number ranging from 21 to 38; and the ratio of PC unit to PD unit is not more than 1:20.

2. The compound of claim 1, which is isolated from the extract of a plant selected from the group consisting of *Graptopetalum* sp., *Rhodiola* ssp. and *Echeveria* sp.

3. The compound of claim 1, which is isolated from *Graptopetalum paraguayense* or *Rhodiola rosea*.

4. A pharmaceutical composition comprising a therapeutically effective amount of the compound of claim 1, and a pharmaceutically acceptable carrier.

5. The pharmaceutical composition of claim 4, which has an anti-cancer activity.

6. A pharmaceutical composition for treatment of liver cancer or liver fibrosis, comprising a therapeutically effect amount of the compound of claim 1, and a pharmaceutically acceptable carrier.

7. The pharmaceutical composition of claim 6, wherein the liver cancer is Hepatocellular carcinoma (HCC).

8. A method for treating liver cancer comprising administrating a subject in need thereof with an therapeutically effective amount of the compound of claim 1.

9. The method of claim 8, wherein the liver cancer is Hepatocellular carcinoma (HCC).

10. A method for treating liver fibrosis comprising administrating a subject in need thereof with an therapeutically effective amount of the compound of claim 1

* * * * *